United States Patent
Boor et al.

(10) Patent No.: US 11,857,789 B2
(45) Date of Patent: *Jan. 2, 2024

(54) NEUROSTIMULATION METHOD AND SYSTEM FOR ACTIVE EMULATION OF PASSIVE DISCHARGE IN PRESENCE OF MRI/EMI INTERFERENCE

(71) Applicant: ADVANCED NEUROMODULATION SYSTEMS, INC., Plano, TX (US)

(72) Inventors: Steven Boor, Plano, TX (US); Daran DeShazo, Lewisville, TX (US)

(73) Assignee: ADVANCED NEUROMODULATION SYSTEMS, INC., Plano, TX (US)

( * ) Notice: Subject to any disclaimer, the term of this patent is extended or adjusted under 35 U.S.C. 154(b) by 379 days.

This patent is subject to a terminal disclaimer.

(21) Appl. No.: 17/186,630

(22) Filed: Feb. 26, 2021

(65) Prior Publication Data

US 2021/0178162 A1 Jun. 17, 2021

Related U.S. Application Data

(63) Continuation of application No. 16/401,943, filed on May 2, 2019, now Pat. No. 10,946,199.

(51) Int. Cl.
*A61N 1/36* (2006.01)
*A61N 1/08* (2006.01)
(Continued)

(52) U.S. Cl.
CPC .......... *A61N 1/36071* (2013.01); *A61N 1/08* (2013.01); *A61N 1/0452* (2013.01); *A61N 1/0456* (2013.01); *A61N 1/0534* (2013.01); *A61N 1/0551* (2013.01)

(58) Field of Classification Search
CPC .......... A61K 2300/00; A61K 2800/591; A61K 36/74; A61K 36/82; A61K 8/97;
(Continued)

(56) References Cited

U.S. PATENT DOCUMENTS 6,609,031 B1 8/2003 Law et al.
7,180,760 B2 2/2007 Varrichio et al.
(Continued)

FOREIGN PATENT DOCUMENTS

WO 2001093953 A1 12/2001

*Primary Examiner* — George Manuel
(74) *Attorney, Agent, or Firm* — Dean D. Small; The Small Patent Law Group, LLC

(57) ABSTRACT

A neurostimulation (NS) system and method are provided. The NS system includes an array of electrodes positioned within a patient. The array of electrodes includes an active electrode. The active electrode is configured to be a cathode electrode located proximate to neural tissue of interest that is associated with a target region. The NS system includes an anode electrode and an electromagnetic interference (EMI) antenna. A control circuit is configured to control delivery of a NS therapy during a therapy delivery interval. The NS therapy is to be delivered between the anode electrode and the active electrode. The NS system develops a residual voltage between the anode electrode and the active electrode over the therapy delivery interval. A current regulator (CR) circuit is connected to the cathode electrode. The CR circuit is configured to control current flow through the cathode electrodes. During a discharge operation, the control circuit is configured to manage the CR circuit to control a discharge current flow over the discharge operation to discharge the residual voltage after therapy delivery in a manner that follows an actively emulated passive discharge (AEPD) profile. During the discharge operation, the CR circuit is connected to the inactive electrode. The CR circuit receives, as a first input, an EMI feedback signal from the EMI antenna. The CR circuit is configured to regulate the discharge current flow through the active electrode based on the EMI feedback signal, to maintain the AEPD profile over the discharge operation while in a presence of an EMI event.

20 Claims, 11 Drawing Sheets

(51) Int. Cl.
*A61N 1/04* (2006.01)
*A61N 1/05* (2006.01)

(58) Field of Classification Search
CPC .. A61K 8/9789; A61N 1/0452; A61N 1/0456;
A61N 1/0534; A61N 1/0551; A61N 1/08;
A61N 1/086; A61N 1/36071; A61N
1/36192; A61Q 19/08
See application file for complete search history.

(56) References Cited

U.S. PATENT DOCUMENTS

| | | |
|---|---|---|
| 7,212,110 B1 | 5/2007 | Martin et al. |
| 7,228,179 B2 | 6/2007 | Campen et al. |
| 7,571,007 B2 | 8/2009 | Erickson et al. |
| 9,054,436 B2 | 6/2015 | Swanson et al. |
| 2006/0170486 A1 | 8/2006 | Tranchina et al. |
| 2012/0330384 A1* | 12/2012 | Perryman .......... A61N 1/37252 607/72 |
| 2018/0085593 A1 | 3/2018 | Fayram et al. |

\* cited by examiner

NEUROSTIMULATION METHOD AND SYSTEM FOR ACTIVE EMULATION OF PASSIVE DISCHARGE IN PRESENCE OF MRI/EMI INTERFERENCE

RELATED APPLICATION

The present application is a continuation application of, and claims priority to, U.S. application Ser. No. 16/401,943, Titled "NEUROSTIMULATION METHOD AND SYSTEM FOR ACTIVE EMULATION OF PASSIVE DISCHARGE IN PRESENCE OF MRI/EMI INTERFERENCE" which was filed on 2 May 2019, the complete subject matter of which is expressly incorporated herein by reference in its entirety.

The present application relates and expressly incorporates herein by reference in its entireties (hereafter referred to as "Co-Pending Related Application"): U.S. patent application Ser. No. 16/401,971, filed 2 May 2019, titled "NEUROSTIMULATION METHOD AND SYSTEM WITH CURRENT REGULATOR BIASED BY FLOATING POWER SUPPLY".

BACKGROUND OF THE INVENTION

Embodiments herein generally relate to neurostimulation (NS) methods and systems and more particularly to regulating current to provide active emulation of passive discharge in the presence of MRI and/or EMI interference.

The use of electronic stimulation systems to control pain or other indications, or to otherwise provide therapy, by nerve or muscle stimulation has been in use for a number of years. For example, spinal cord stimulation (SCS) is a technique that has been used for pain management since the 1960s. Of course, stimulation systems may be used in stimulating areas other than the spinal cord, such as for deep brain stimulation (DBS), muscle stimulation, etc.

Stimulation systems often comprise a pulse generator coupled to one or more percutaneous leads having a plurality of electrodes disposed in an area in which neurostimulation is desired. Alternatively, stimulation systems may comprise micro-stimulation systems in which a small implantable housing having electrodes thereon includes a pulse generator, wherein the entire micro-stimulation system is disposed in an area in which neurostimulation is desired. Of course, all or a portion of a stimulation system need not be implanted into a body to provide a desired therapy.

A stimulation system pulse generator may be provided in various configurations, such as a totally implanted pulse generator (IPG) or a radio frequency (RF) system. A typical IPG configuration comprises a surgically implanted, internally-powered pulse generator and multi-electrode lead. A typical RF system configuration comprises a surgically implanted, passive receiver and a transmitter which is worn externally. In operation, the transmitter communicates, through an RF signal, to the implanted receiver to provide stimulation energy and control.

Electrodes used with the foregoing pulse generators deliver a particularized electric field to a specific region of the spinal cord or surrounding tissue. Applying such an electric field across one or more nerve bundles and/or nerve roots, if properly directed and produced at the necessary levels, can "mask" certain forms of chronic pain. Similarly, applying an electric field across other tissue, such as muscle or brain matter, near which such electrodes are disposed may provide a desired therapy. The focus, characteristics and intensity of the generated electric field are determined by the electrode configuration (the polarity, if any, assumed by each electrode) and the electric pulse waveform (collectively "stimulation setting"). The waveform properties generally include a stimulation frequency, a stimulation pulse width, and stimulation amplitude information.

Implantation of all or a portion of a stimulation system, e.g., a stimulation system including a fully implanted IPG or a RF system receiver/transmitter, necessarily requires a neurostimulation patient to undergo an implantation surgery. Additionally, routing a lead sub-dermally between an implanted pulse generator and the tissue area to be stimulated typically requires a relatively invasive procedure, such as a tunneling procedure. Likewise, explanting all or a portion of a stimulation system requires a neurostimulation patient to again undergo the trauma of surgery.

However, conventional IPGs experience certain limitations, particularly in the presence of electromagnetic interference (EMI) including, but not limited to magnetic resonance imaging EM fields. For example, when a patient, who has an implanted IPG, undergoes an MRI scan, the EMI from the MRI system may generate unwanted voltage potentials within the IPG and across the electrodes of the NS lead. Among other issues, if the IPG continues to attempt to deliver an NS therapy while a patient is undergoing an MRI scan, the EM fields from the MRI scanner may induce added voltage potentials across the electrodes, thereby changing the magnitude and nature of the NS therapy in unpredictable, undesired and uncontrollable manners.

FIG. 9 illustrates an example for current signals experienced at select points in a conventional IPG that is attempting to deliver an NS therapy in the presence of EMI. The timing diagram plots current flow along the vertical axis at various points within the IPG and time along the horizontal axis. The upper current signal, denoted I_RSCALE, represents a target current profile to be delivered to tissue during a stimulation pulse 902 of a desired therapy. The example NS therapy target stimulation current pulse 902 has a pulse amplitude of 2 mA and a pulse width of 90 μs. In general, it is desirable that the IPG does not introduce any other currents to flow through the patient other than the NS therapy current pulses and the necessary charge-balancing discharge current after stimulation, even while in the presence of EMI, such as during an MRI scan.

During delivery of the stimulation current pulse 902, anode and cathode electrodes of the IPG are connected to a therapy delivery circuit that controls the timing and shape of the stimulation current pulse 902. Following delivery of the stimulation current pulse 902, a conventional IPG closes a discharge switch which shorts together the anode and cathode electrodes utilized to deliver the stimulation current pulse 902, in order to achieve a charge balanced state for the stimulation electrodes (which is necessary for patient safety and electrode material integrity). However, in a conventional IPG, once the discharge switch is closed, the IPG may potentially allow EMI fields (to which the IPG leads and Case are exposed) to cause an interference current to flow through the patient. This is especially problematic for NS therapies which utilize the IPG Can or Case as a stimulation electrode (commonly referred to as a Monopolar stimulation configuration), which is the preferred and most energy-efficient stimulation configuration used for DBS therapies. FIG. 9 also illustrates for a conventional IPG examples of interference currents experienced by the patient at the stimulation anode and cathode in a Monopolar stimulation configuration, denoted at I_CASE and I_TISSUE. As a non-limiting example, the interference currents are illustrated generally as sine or cosine waves, generally denoting unpredictable, uncontrolled or undesirable current flow through the patient, that may occur before and after the stimulation current pulse 902 (as the discharge switch is only closed before and after the stimulation current pulse 902 is delivered, not during stimulation).

To avoid an unpredictable, uncontrolled or undesirable current flow before and after stimulation current pulses of the NS therapy, many NS systems have stimulation therapy turned off during an MRI scan. Additionally or alternatively, the IPG may be programmed to include a separate or special NS therapy that is configured specifically for the purpose of being utilized during the presence of an MRI scan, as for example the use of a Bipolar configuration of electrodes which avoids the use of the IPG Can or Case as a stimulation electrode. Adding an NS therapy tailored to be utilized primarily during an MRI scan introduces an undesired additional burden in programming of the IPG, as well as may require additional memory and/or circuitry to implement the MRI specific NS therapy.

A goal continues to remain to improve performance of NS systems, particularly in the presence of EMI. Among other things, it is desirable to reduce the physical circuit area and complexity of electronic control circuits.

A need remains for improved methods and systems for delivering consistent, intended, and predictable therapy and for managing discharge of voltage buildups on electrodes, even while in the presence of EMI events, such as an MRI scanner.

SUMMARY

In accordance with embodiments herein, a neurostimulation (NS) system is provided. The NS system includes an array of electrodes positioned within a patient. The array of electrodes includes an active electrode. The active electrode is configured to be a cathode electrode located proximate to neural tissue of interest that is associated with a target region. The NS system includes an anode electrode and an electromagnetic interference (EMI) antenna. A control circuit is configured to control delivery of a NS therapy during a therapy delivery interval. The NS therapy is to be delivered between the anode electrode and the active electrode. The NS system develops a residual voltage between the anode electrode and the active electrode over the therapy delivery interval. A current regulator (CR) circuit is connected to the cathode electrode. The CR circuit is configured to control current flow through the cathode electrodes. During a discharge operation, the control circuit is configured to manage the CR circuit to control a discharge current flow over the discharge operation to discharge the residual voltage after therapy delivery in a manner that follows an actively emulated passive discharge (AEPD) profile. During the discharge operation, the CR circuit is connected to the EMI antenna. The CR circuit receives, as a first input, an EMI feedback signal from the EMI antenna. The CR circuit is configured to regulate the discharge current flow through the active electrode and anode electrode based on the EMI feedback signal, to maintain the AEPD profile over the discharge operation while in a presence of an EMI event.

Optionally, the EMI feedback signal may be indicative of a voltage interference induced at least in part by an electromagnetic field surrounding the NS system. The EMI antenna may include at least one of: i) an inactive electrode from the array of electrodes, or ii) a non-electrode wire. The non-electrode wire is provided within a lead or routed with insulation substantially alongside the outside of a lead that includes the array of electrodes provided at a distal end of the lead. A reference voltage source may be configured to supply a reference voltage as a second input to the CR circuit. The CR circuit may be configured to regulate the current flow through the active and anode electrodes based on a difference between the EMI feedback signal and the reference voltage. The CR circuit may comprise an error amplifier and a transistor. The error amplifier may be configured to hold the EMI feedback signal at a reference voltage and provide an output based thereon. The transistor may be configured to regulate the current flow through the active and anode electrodes based on the output of the error amplifier to maintain the AEPD profile while in the presence of the EMI event.

Optionally, the EMI antenna may include an inactive electrode where the inactive electrode and the active electrode may be configured to have substantially similar electrical properties. The NS system may include a lead having a distal end that may include the array of electrodes. The EMI antenna may include a non-electrode wire within the lead or routed with insulation substantially alongside the outside of the lead. The control circuit and CR circuit may be enclosed within a housing of an implantable pulse generator. The control circuit may be configured to deliver the NS therapy repeatedly over successive therapy delivery intervals that are separated by corresponding successive discharge operations while in the presence of the EMI event. The CR circuit may be configured to modulate the current flow over the discharge operation, based on the EMI feedback signal, in order to follow the AEPD profile to compensate for voltage fluctuation caused by the EMI event.

In accordance with embodiments herein, a method for managing neurostimulation (NS) is provided. The method provides an array of electrodes to be located proximate to neural tissue of interest that is associated with a target region. The array of electrodes includes an active electrode configured to be a cathode electrode. The method delivers a NS therapy during a therapy delivery interval between an anode electrode and the active electrode. The NS system develops a residual voltage between the anode electrode and the active electrode over the therapy delivery interval. During a discharge operation in a presence of an EMI event the method controls a discharge current flow over the discharge operation to discharge the residual voltage after therapy delivery in a manner that follows an actively emulated passive discharge (AEPD) profile. The method obtains an electromagnetic interference (EMI) feedback signal from an EMI antenna while in the presence of the EMI event and regulates the discharge current flow through the anode and cathode electrodes based on the EMI feedback signal to maintain the AEPD profile over the discharge operation while in the presence of the EMI event.

Optionally, the EMI feedback signal may be indicative of a voltage interference induced at least in part by an electromagnetic field surrounding the NS system. The interference voltage gradient may be induced between the EMI antenna and the anode electrode. The NS method may include supplying a reference voltage, and regulating the current flow based on a difference between the EMI feedback signal and the reference voltage. The controlling operation may utilize a current regulator (CR) circuit that comprises an error amplifier and a transistor. The NS method may compare the EMI feedback signal to a reference voltage at the error amplifier and provide an output based thereon and may utilize the transistor to regulate the discharge current flow through the anode and cathode electrodes based on the output of the error amplifier to maintain the AEPD profile while in the presence of the EMI event.

Optionally, the NS method may utilize an inactive electrode as the EMI antenna and configure the inactive electrode and the active electrode to have substantially similar electrical properties. The NS method may implant a lead having a distal end that includes the array of electrodes. The NS method may implant an implantable pulse generator that houses a control circuit and current regulator (CR) circuit that deliver the NS therapy and control the discharge current flow during the discharge operation. The delivering operation may further comprise delivering the NS therapy repeatedly over successive therapy delivery intervals that are separated by corresponding successive discharge operations while in the presence of the EMI event. The regulating operation may further comprise compensating for voltage fluctuation caused by the EMI event by modulating the discharge current flow over the discharge operation, based on the EMI feedback signal, in order to follow the AEPD profile.

DETAILED DESCRIPTION

Figure 1:
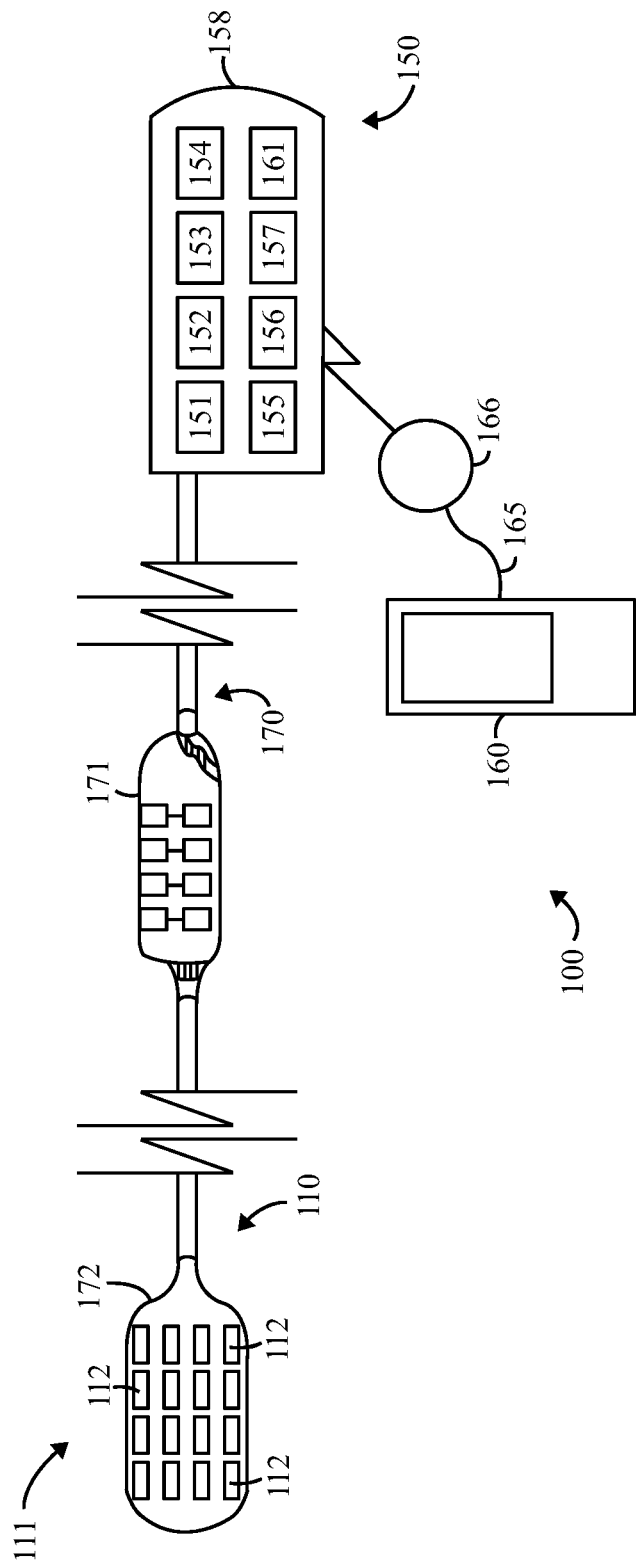
FIG. 1 depicts a schematic block diagram of an embodiment of a neurostimulation system.
Figure 2A:
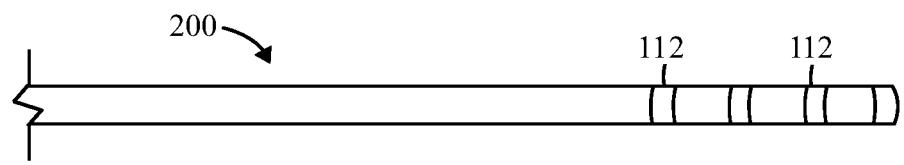
FIG. 2A respectively depicts stimulation portions of embodiments for inclusion at the distal end of a lead.
Figure 2B:
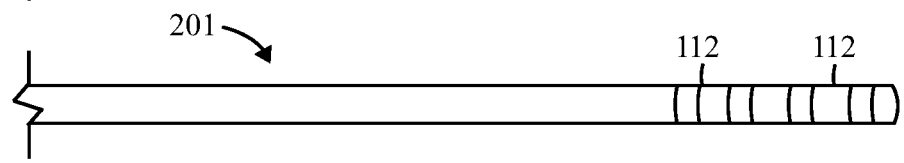
FIG. 2B respectively depicts stimulation portions of embodiments for inclusion at the distal end of a lead.
Figure 2C:
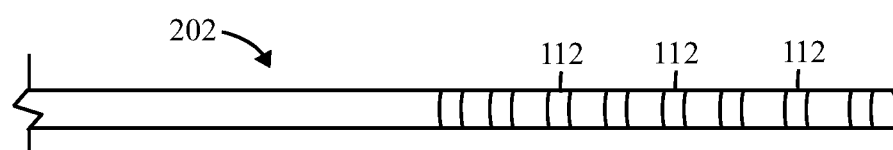
FIG. 2C respectively depicts stimulation portions of embodiments for inclusion at the distal end of a lead.
Figure 2D:
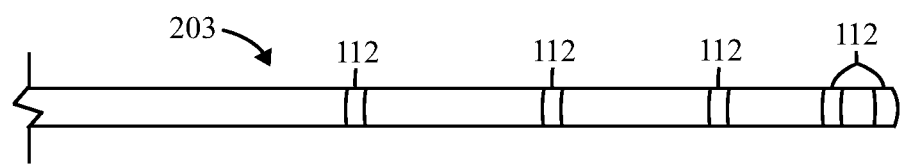
FIG. 2D respectively depicts stimulation portions of embodiments for inclusion at the distal end of a lead.
Figure 2E:
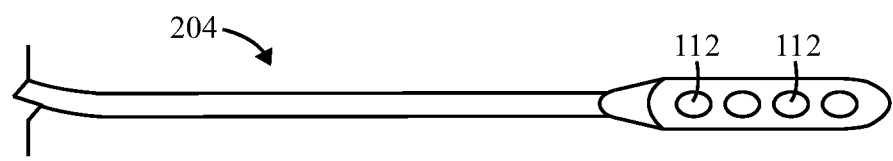
FIG. 2E respectively depicts stimulation portions of embodiments for inclusion at the distal end of a lead.
Figure 2F:
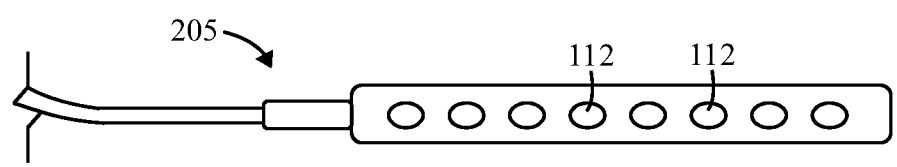
FIG. 2F respectively depicts stimulation portions of embodiments for inclusion at the distal end of a lead.
Figure 2G:
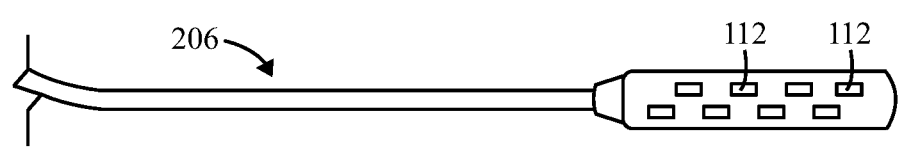
FIG. 2G respectively depicts stimulation portions of embodiments for inclusion at the distal end of a lead.
Figure 2H:
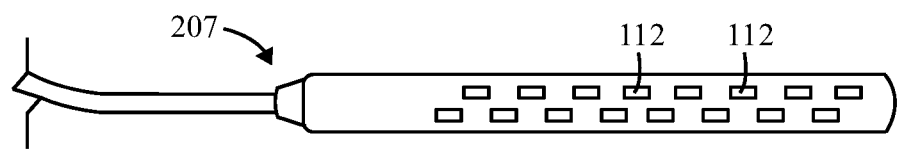
FIG. 2H respectively depicts stimulation portions of embodiments for inclusion at the distal end of a lead.
Figure 2I:
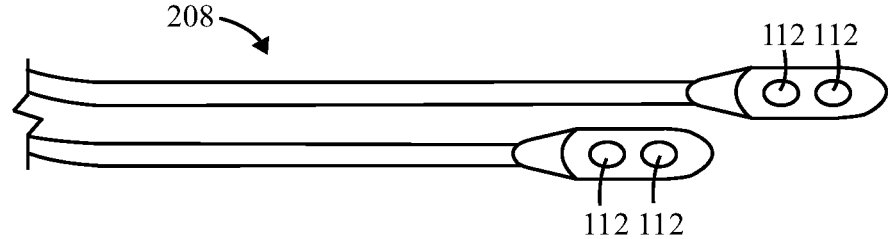
FIG. 2I respectively depicts stimulation portions of embodiments for inclusion at the distal end of a lead.

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

Embodiments herein describe a neurostimulation (NS) system configured to deliver NS therapy to a target region within a patient. The NS therapy is defined by one or more stimulation parameters. The NS therapy is delivered proximate to neural tissue of interest that is associated with a target region.

Terms

"Stimulation parameters" refer to electrical characteristics of the NS therapy. The stimulation parameters may represent a pulse width, a frequency, an amplitude, a duty cycle, an NS therapy type, and/or the like. The NS therapy type can represent a characteristic of the NS therapy delivered by the NS system. The characteristic may correspond to stimulation and/or pulse patterns of the NS therapy. The pulse patterns may be a burst stimulation waveform or a tonic stimulation waveform of the NS therapy. The tonic stimulation waveform represents a pulse repeated at a rate defined by the duty cycle. The burst stimulation waveform represents a series of pulses grouped to form a pulse train. The pulse train may be repeated at a cycle rate defined by the duty cycle.

The term "active," when referring to an electrode, shall mean a stimulation electrode that is utilized to deliver stimulation in connection with one or more types of therapy for the present patient.

The term "inactive," when referring to an electrode, shall mean an unused, non-stimulation electrode that is not used to deliver stimulation in connection with any type of therapy for the present patient. The inactive electrode may also be referred to as an unused or non-stimulation electrode as no therapy is delivered through the electrode. As explained herein, one or more inactive electrodes are used as part of a feedback control loop in connection with substantially minimizing MRI/EMI induced stimulation interference.

The terms "electromagnetic interference" and "EMI" shall mean interference experienced by an NS system when exposed to electromagnetic fields. One non-limiting example is when an NS system is in the presence of a magnetic resonance imaging (MRI) field, the NS system will experience EMI.

The terms "actively emulated passive discharge profile" and "AEPD profile" refer to a shape of a curve plotting charge, voltage and/or current over time while discharging a residual voltage built upon across a load and/or between anode and cathode electrodes of an NS system.

The terms "non-electrode wire" and "dummy wire" shall mean a conductor provided within a stimulation lead or routed with insulation substantially alongside the outside of a stimulation lead that is coupled (at a proximal end) to a current regulator circuit (as described herein) and is not coupled to an electrode at the distal end. By way of example, the non-electrode wire may have a distal end that is allowed to electrically float relative to the human tissue, and a proximal end which connects to a current regulator circuit in a NS system. The non-electrode wire may be located at an intermediate and/or distal portion of a body of the lead alongside other conductive wires that are coupled to the electrodes utilized by the NS system. The non-electrode wire may be enclosed within the lead or routed with insulation substantially alongside the outside of the lead body to avoid direct electrical contact with human tissue.

Overview

In accordance with embodiments herein, methods and systems implement a current regulator (CR) circuit that exhibits very efficient performance, while utilizing a limited circuit area utilized within the NS system and provides a relatively non-complex electronic control circuit. The CR circuit provides an improved and optimized control architecture for active emulation of passive discharge in the presence of EMI.

Embodiments herein provide a compact and efficient current regulator circuit that affords an advantageous imitation scheme for achieving numerous advancements in connection with implementing an actively emulated passive discharge. Embodiments herein implement the actively emulated passive discharge even while in the presence of MRI scans and other EMI events, thereby enabling continuous delivery of deep brain stimulation therapy, such as in connection with patients experiencing debilitating motion disorders and other brain disorders.

Embodiments herein build upon and highly optimize actively emulated passive discharge configurations. Among other things, methods and systems herein utilize a self-contained current regulator circuit architecture for controlling an exponentially decreasing discharge current. Embodiments herein control the discharge current in a manner that alleviates the need for any kind of model extraction of an IPG load. Embodiments herein further alleviate the need to determine an initial discharge current or to determine discharge control parameters that may be otherwise appropriate for an actively emulated passive discharge control circuit program specifically for use while in the presence of a particular type of MRI field strength or scan type.

An EMI antenna can be utilized to sense and mitigate interference voltages induced by EMI. By way of example, the EMI antenna may include one or more Kelvin connect electrodes or unused electrodes in a lead that are not being used to deliver stimulation therapy to the patient. The unused electrode can operate as the EMI antenna to sense and mitigate interference voltages induced by EMI. Additionally or alternatively, the EMI antenna may be constructed as a "dummy" wire (also referred to as a non-electrode wire) provided within the lead or routed with insulation substantially alongside the outside of the lead and arranged to extend alongside other stimulation wires in the lead. The dummy wire may not electrically conduct with human tissue, and thus may not be considered to be an "electrode."

Among other things, embodiments herein utilize the insight that, during an MRI scan or other type of EMI event (collectively EMI), the interference voltages induced on each electrode of a DBS lead are very similar (e.g., nearly identical) and/or exhibit a common mode characteristic to all electrodes. More specifically, the EMI induces similar voltage variations at each of the electrodes at any given instant in time. Embodiments herein utilize the foregoing point by designating an inactive or unused electrode, of a neural stimulation lead, to provide a feedback control signal to the current regulator circuit. As a nonlimiting example, the unused electrode may be configured as a "Kelvin connection" electrode. The feedback control signal is utilized by the current regulator circuit for simple, effective and efficient control of an actively emulated passive discharge. The feedback control, via a Kelvin connection electrode, is highly effective at canceling out interference voltages induced by EMI, as well as greatly simplifying an implementation of the AEPD operation and eliminates the need for numerous other structures, such as an IPG load calculation, excess memory storage for EMI related discharge parameters or settings, a complex discharge control state machine and/or extensive computations for the imitation and control of the AEPD operation while in the presence of EMI.

FIG. 1 depicts a schematic block diagram of an embodiment of a neurostimulation (NS) system 100. The NS system 100 is configured to generate electrical pulses (e.g., excitation pulses) for application to neural tissue of the patient according to one embodiment. For example, the NS system 100 may be adapted to stimulate spinal cord tissue, dorsal root, dorsal root ganglion (DRG), peripheral nerve tissue, deep brain tissue, cortical tissue, cardiac tissue, digestive tissue, pelvic floor tissue, and/or any other suitable neural tissue of interest within a body of a patient.

The NS system 100 includes an implantable pulse generator (IPG) 150 that is adapted to generate electrical pulses for application to tissue of a patient. The IPG 150 typically comprises a metallic housing or can 158 that encloses a controller circuit 151, pulse generating circuitry 152, a charging coil 153, a battery 154, a communication circuit 155, battery charging circuitry 156, switching circuitry 157, memory 161, and/or the like. The communication circuit 155 may represent hardware that is used to transmit and/or receive data along a uni-directional communication link and/or bi-directional communication link (e.g., with an external device 160).

The controller circuit 151 is configured to control the operation of the IPG 150. The controller circuit 151 may include one or more processors, a central processing unit (CPU), one or more microprocessors, or any other electronic component capable of processing input data according to program instructions. Optionally, the controller circuit 151 may include and/or represent one or more hardware circuits or circuitry that include, are connected with, or that both include and are connected with one or more processors, controllers, and/or other hardware logic-based devices. Additionally or alternatively, the controller circuit 151 may execute instructions stored on a tangible and non-transitory computer readable medium (e.g., the memory 161).

The IPG 150 may include a separate or an attached extension component 170. The extension component 170 may be a separate component. For example, the extension component 170 may connect with a "header" portion of the IPG 150, as is known in the art. If the extension component 170 is integrated with the IPG 150, internal electrical connections may be made through respective conductive components. Within the IPG 150, electrical pulses are generated by the pulse generating circuitry 152 and are provided to the switching circuitry 157. The switching circuitry 157 connects to outputs of the IPG 150. Electrical connectors (e.g., "Bal-Seal" connectors) within the connector portion 171 of the extension component 170 or within the IPG header may be employed to conduct various stimulation pulses. The terminals of one or more leads 110 are inserted within the connector portion 171 or within the IPG header for electrical connection with respective connectors. The pulses originating from the IPG 150 are provided to the one or more leads 110. The pulses are then conducted through the conductors of the lead 110 and applied to tissue of a patient via an electrode array 111. Any suitable known or later developed design may be employed for connector portion 171.

The electrode array 111 may be positioned on a paddle structure of the lead 110. For example, in a planar formation on a paddle structure as disclosed in U.S. Provisional Application No. 61/791,288, entitled, "PADDLE LEADS FOR NEUROSTIMULATION AND METHOD OF DELIVERYING THE SAME," which is expressly incorporated herein by reference. The electrode array 111 includes a plurality of electrodes 112 aligned along corresponding rows and columns. Each of the electrodes 112 are separated by non-conducting portions of the paddle structure, which electrically isolate each electrode 112 from an adjacent electrode 112. The non-conducting portions may include one or more insulative materials and/or biocompatible materials to allow the lead 110 to be implantable within the patient. Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane. The electrodes 112 may be configured to emit pulses in an outward direction.

Optionally, the IPG 150 may have one or more leads 110 connected via the connector portion 171 of the extension component 170 or within the IPG header. For example, a DRG stimulator, a steerable percutaneous lead, and/or the like. Additionally or alternatively, the electrodes 112 of each lead 110 may be configured separately to emit excitation pulses.

Leads

FIGS. 2A-2I, respectively, depict stimulation portions 200-208 for inclusion at the distal end of the lead 110. For example, the stimulation portions 200-208 depict a conventional stimulation portion of a "percutaneous" lead with multiple electrodes 112. The stimulation portions 200-208 depict a stimulation portion including several segmented electrodes 112. Example fabrication processes are disclosed in U.S. patent application Ser. No. 12/895,096, entitled, "METHOD OF FABRICATING STIMULATION LEAD FOR APPLYING ELECTRICAL STIMULATION TO TISSUE OF A PATIENT," which is incorporated herein by reference. Stimulation portions 204-208 include multiple electrodes 112 on alternative paddle structures than shown in FIG. 1.

In connection to FIG. 1, the lead 110 may include a lead body 172 of insulative material about a plurality of conductors within the material that extend from a proximal end of lead 110, proximate to the IPG 150, to its distal end. The conductors electrically couple a plurality of the electrodes 112 to a plurality of terminals (not shown) of the lead 110. The terminals are adapted to receive electrical pulses and the electrodes 112 are adapted to apply the pulses to the stimulation target of the patient. It should be noted that although the lead 110 is depicted with twenty electrodes 112, the lead 110 may include any suitable number of electrodes 112 (e.g., less than twenty, more than twenty) as well as terminals, and internal conductors.

Although not required for all embodiments, the lead body 172 of the lead 110 may be fabricated to flex and elongate upon implantation or advancing within the tissue (e.g., nervous tissue) of the patient towards the stimulation target and movements of the patient during or after implantation. By fabricating the lead body 172, according to some embodiments, the lead body 172 or a portion thereof is capable of elastic elongation under relatively low stretching forces. Also, after removal of the stretching force, the lead body 172 may be capable of resuming its original length and profile. For example, the lead body may stretch 10%, 20%, 25%, 35%, or even up or above to 50% at forces of about 0.5, 1.0, and/or 2.0 pounds of stretching force. Fabrication techniques and material characteristics for "body compliant" leads are disclosed in greater detail in U.S. Provisional Patent Application No. 60/788,518, entitled "Lead Body Manufacturing," which is expressly incorporated herein by reference.

For implementation of the components within the IPG 150, a processor and associated charge control circuitry for an IPG is described in U.S. Pat. No. 7,571,007, entitled "SYSTEMS AND METHODS FOR USE IN PULSE GENERATION," which is expressly incorporated herein by reference. Circuitry for recharging a rechargeable battery (e.g., battery charging circuitry 156) of an IPG using inductive coupling and external charging circuits are described in U.S. Pat. No. 7,212,110, entitled "IMPLANTABLE DEVICE AND SYSTEM FOR WIRELESS COMMUNICATION," which is expressly incorporated herein by reference.

An example and discussion of "constant current" pulse generating circuitry (e.g., pulse generating circuitry 152) is provided in U.S. Patent Publication No. 2006/0170486 entitled "PULSE GENERATOR HAVING AN EFFICIENT FRACTIONAL VOLTAGE CONVERTER AND METHOD OF USE," which is expressly incorporated herein by reference. One or multiple sets of such circuitry may be provided within the IPG 150. Different pulses on different electrodes 112 may be generated using a single set of the pulse generating circuitry 152 using consecutively generated pulses according to a "multi-stimset program" as is known in the art. Complex stimulation parameters may be employed such as those described in U.S. Pat. No. 7,228,179, entitled "Method and apparatus for providing complex tissue stimulation patterns," and International Patent Publication Number WO 2001/093953 A1, entitled "NEUROMODULATION THERAPY SYSTEM," which are expressly incorporated herein by reference. Alternatively, multiple sets of such circuitry may be employed to provide pulse patterns (e.g., the tonic stimulation waveform, the burst stimulation waveform) that include generated and delivered stimulation pulses through various electrodes 112 of the one or more leads 110 as is also known in the art. Various sets of stimulation parameters may define the characteristics and timing for the pulses applied to the various electrodes 112 as is known in the art. Although constant excitation pulse generating circuitry is contemplated for some embodiments, any other suitable type of pulse generating circuitry may be employed such as constant voltage pulse generating circuitry.

Figure 3:
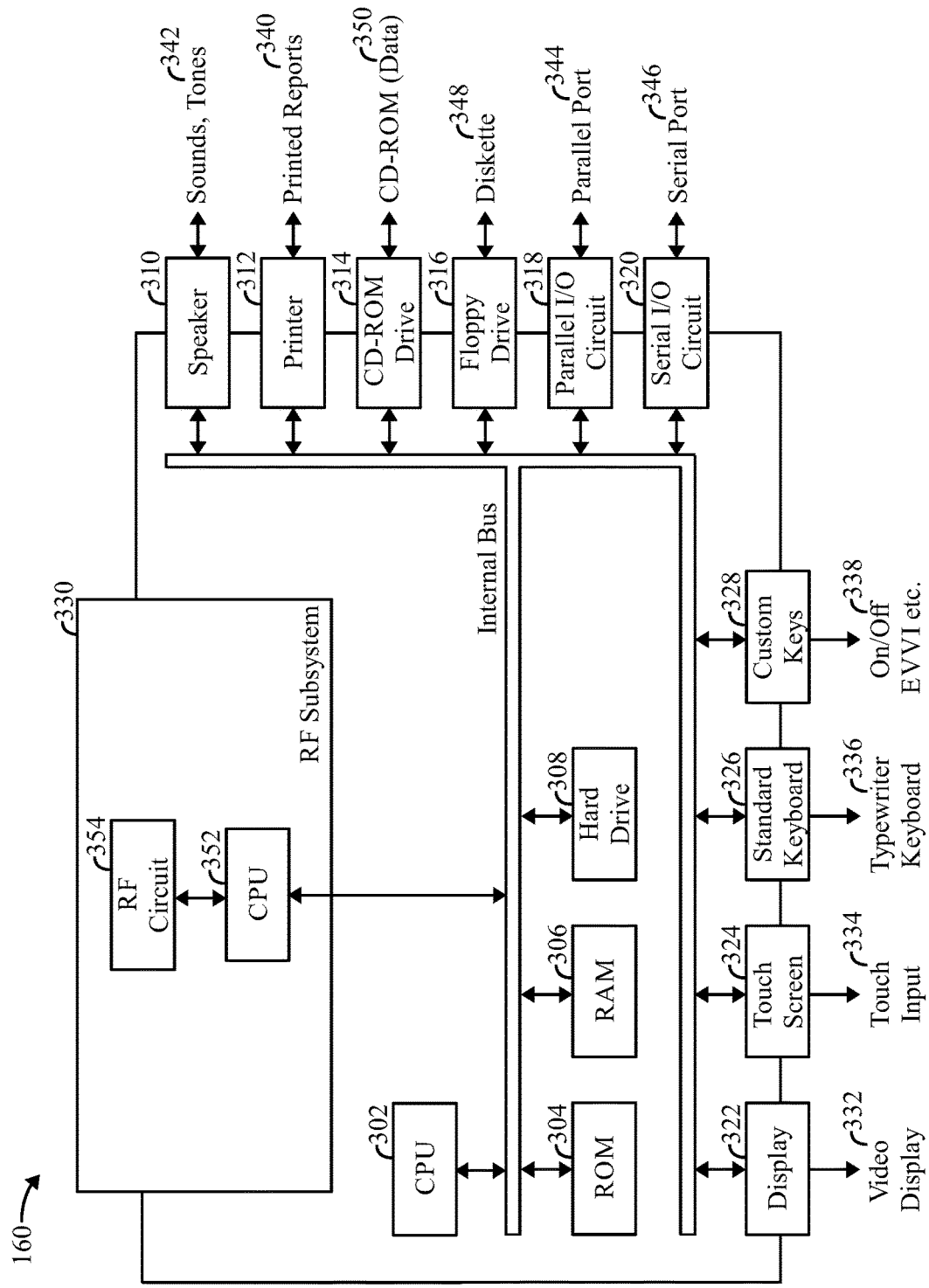
FIG. 3 depicts a schematic block diagram of an embodiment of the external device 160.

The external device 160 may be implemented to charge/recharge the battery 154 of the IPG 150 (although a separate recharging device could alternatively be employed), to access the memory 161, to program the IPG 150 when implanted within the patient, to communicate triggering events to the NS system 100, and/or the like. FIG. 3 depicts a schematic block diagram of an embodiment of the external device 160. The external device 160 may be a workstation, a portable computer, an NS system programmer, a PDA, a cell phone, a smart phone, a tablet, and/or the like.

FIG. 3 illustrates a block diagram of an external device formed in accordance with embodiments herein. The external device 160 includes an internal bus that connects/interfaces with a Central Processing Unit (CPU) 302, ROM 304, RAM 306, a hard drive 308, a speaker 310, a printer 312, a CD-ROM drive 314, a floppy drive 316, a parallel I/O circuit 318, a serial I/O circuit 320, a display 322, a touch screen 324, a standard keyboard connection 326, custom keys 328, and a radio frequency (RF) subsystem 330. The internal bus is an address/data bus that transfers information between the various components described herein. The hard drive 308 may store operational programs as well as data, such as waveform templates and detection thresholds.

The CPU 302 is configured to control the operation of the external device 160. The CPU 302 may include one or more processors. Optionally, the CPU 302 may include one or more microprocessors, a graphics processing unit (GPU), or any other electronic component capable of processing inputted data according to specific logical instructions. Optionally, the CPU 302 may include and/or represent one or more hardware circuits or circuitry that include, are connected with, or that both include and are connected with one or more processors, controllers, and/or other hardware logic-based devices. Additionally or alternatively, the CPU 302 may execute instructions stored on a tangible and non-transitory computer readable medium (e.g., the ROM 304, the RAM 306, hard drive 308).

Optionally, the CPU 302 may include RAM or ROM memory, logic and timing circuitry, state machine circuitry, and/or I/O circuitry to interface with the NS system 100. The display 322 may be connected to a video display 332. The touch screen 324 may display graphic information relating to the NS system 100. The display 322 displays various information related to the processes described herein.

The touch screen 324 accepts a user's touch input 334 when selections are made. The keyboard 326 (e.g., a typewriter keyboard 336) allows the user to enter data to the displayed fields, as well as interface with the RF subsystem 330. The touch screen 324 and/or the keyboard 326 is configured to allow the user to operate the NS system 100. The external device 160 may be controlled by the user (e.g., doctor, clinician, patient) through the touch screen 324 and/or the keyboard 326 allowing the user to interact with the NS system 100. The touch screen 324 and/or the keyboard 326 may permit the user to move electrical stimulation along and/or across one or more of the lead(s) 110 using different electrode 112 combinations, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME," which is expressly incorporated herein by reference. Optionally, the touch screen 324 and/or the keyboard 326 may permit the user to designate which electrodes 112 are to stimulate (e.g., emit excitation pulses, in an anode state, in a cathode state) the stimulation target.

Custom keys 328 turn on/off 338 the external device 160. The printer 312 prints copies of reports 340 for a physician to review or to be placed in a patient file, and the speaker 310 provides an audible warning (e.g., sounds and tones 342) to the clinician and/or patient. The parallel I/O circuit 318 interfaces with a parallel port 344. The serial I/O circuit 320 interfaces with a serial port 346. The floppy drive 316 accepts diskettes 348. Optionally, the floppy drive 316 may include a USB port or other interface capable of communicating with a USB device such as a memory stick. The CD-ROM drive 314 accepts CD ROMs 350.

The RF subsystem 330 includes a central processing unit (CPU) 352 in electrical communication with an RF circuit 354. The RF subsystem 330 is configured to receive and/or transmit information with the NS system 100. The RF subsystem 330 may represent hardware that is used to transmit and/or receive data along a uni-directional and/or bi-directional communication link. The RF subsystem 330 may include a transceiver, receiver, transceiver and/or the like and associated circuitry (e.g., antennas) for wirelessly communicating (e.g., transmitting and/or receiving) with the NS system 100. For example, protocol firmware for transmitting and/or receiving data along the uni-directional and/or bi-directional communication link may be stored in the memory (e.g., the ROM 304, the RAM 306, the hard drive 308), which is accessed by the CPU 352. The protocol firmware provides the network protocol syntax for the CPU 352 to assemble data packets, establish and/or partition data received along the uni-directional and/or bi-directional communication links, and/or the like. The uni-directional and/or bi-directional communication link can represent a wireless communication (e.g., utilizing radio frequency (RF)) link for exchanging data (e.g., data packets) between the NS system 100 and the external device 160. The uni-directional and/or bi-directional communication link may be based on a customized communication protocol and/or a standard communication protocol, such as Bluetooth, NFC, RFID, GSM, infrared wireless LANs, HIPERLAN, 3G, LTE, and/or the like.

Additionally or alternatively, the RF subsystem 330 may be operably coupled to a "wand" 165 (FIG. 1). The wand 165 may be electrically connected to a telemetry component 166 (e.g., inductor coil, RF transceiver) at the distal end of wand 165 through respective wires (not shown) allowing bi-directional communication with the NS system 100. For example, the user may initiate communication with the NS system 100 by placing the wand 165 proximate to the NS system 100. Preferably, the placement of the wand 165 allows the telemetry system of the wand 165 to be aligned with the communication circuit 155.

Also, the external device 160 may permit operation of the IPG 150 according to one or more NS programs or therapies to treat the patient. For example, the NS program corresponds to the NS therapy and/or executed by the IPG 150. Each NS program may include one or more sets of stimulation parameters of the pulses including pulse amplitude, stimulation level, pulse width, pulse frequency or inter-pulse period, pulse repetition parameter (e.g., number of times for a given pulse to be repeated for respective stimset during execution of program), biphasic pulses, monophasic pulses, etc. The IPG 150 may modify its internal parameters in response to the control signals from the external device 160 to vary the stimulation characteristics of the stimulation pulses transmitted through the lead 110 to the tissue of the patient. NS systems, stimsets, and multi-stimset programs are discussed in PCT Publication No. WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are expressly incorporated herein by reference.

Figure 4:
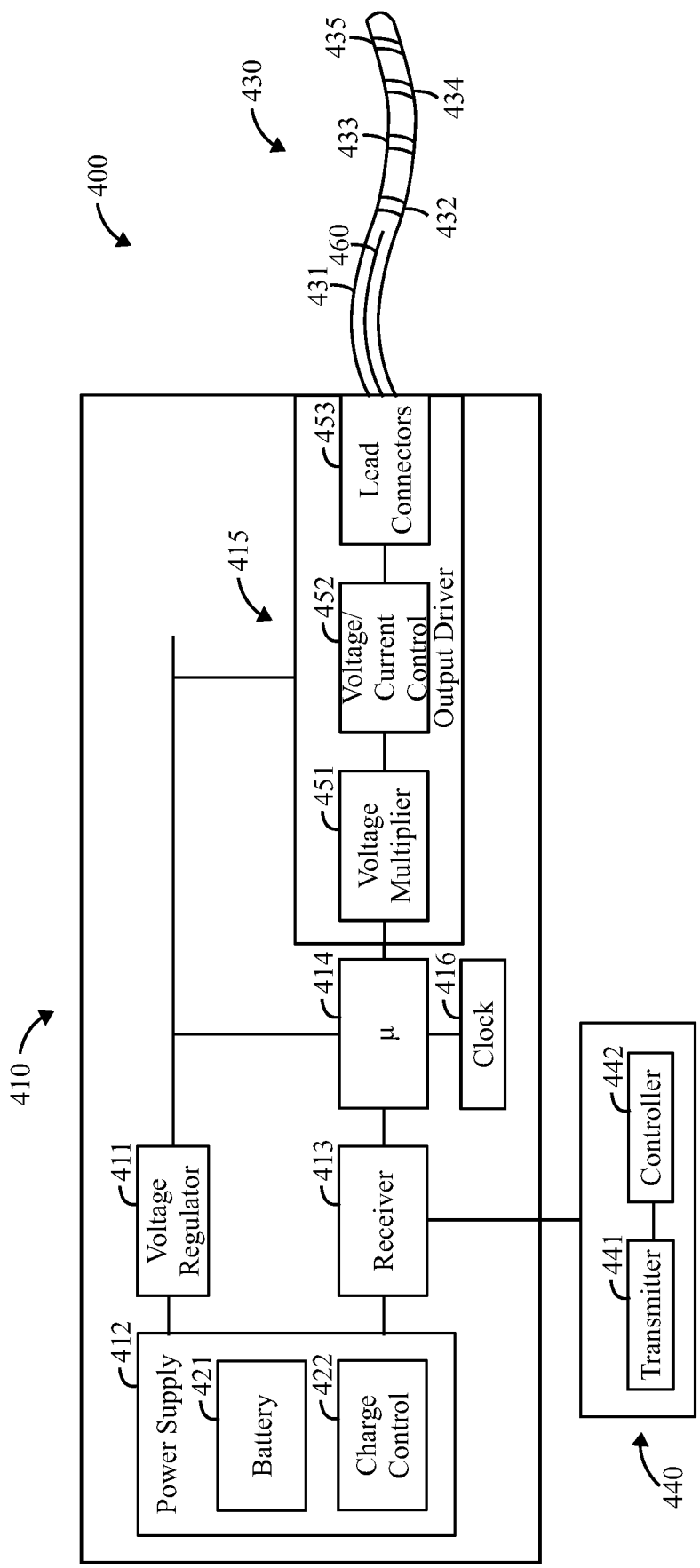
FIG. 4 illustrates a stimulation system adapted according to an embodiment and is shown in a high-level functional block diagram.

Directing attention to FIG. 4, stimulation system 400 is adapted according to an embodiment and is shown in a high-level functional block diagram. In operation, stimulation system 400 generates and applies a stimulus to tissue or a certain location of a body. Stimulation system 400 of the illustrated embodiment includes a generator portion, shown as implantable pulse generator (IPG) 410, providing a stimulation or energy source, stimulation portion, shown as lead 430, for application of the stimulus pulse(s), and an optional external controller, shown as programmer/controller 440, to program and/or control implantable pulse generator 410 via a wireless communications link. IPG 410 may be implanted within a living body (not shown) for providing electrical stimulation from IPG 410 to a selected area of the body via lead 430, perhaps under control of external programmer/controller 440. It should be appreciated that, although lead 430 is illustrated to provide a stimulation portion of stimulation system 400 configured provide stimulation remotely with respect to the generator portion of stimulation system 400, a lead as described herein is intended to encompass a variety of stimulation portion configurations. For example, lead 430 may comprise a microstimulator electrode disposed adjacent to a generator portion. Furthermore, a lead configuration may include more (e.g., 8, 16, 32, etc.) or fewer (e.g., 1, 2, etc.) electrodes than those represented in the illustrations. As explained herein, the lead 430 may include an EMI antenna configured to provide an EMI feedback signal indicative of an amount of interference voltage induced by the EMI. The EMI antenna may be implemented in various manners, such as utilizing an inactive electrode (e.g., one of electrodes 432-435) and/or utilizing a non-electrode segment of wire 460 provided within the lead or routed with insulation substantially alongside the outside of the lead 430. The wire 460 is not connected to any of the electrodes 432-435 and may be held within a body of the lead 430 to prevent the wire 460 from contacting human tissue. Alternatively, the wire 460 may be fully insulated and routed substantially alongside the outside of the lead 430.

IPG 410 may comprise a self-contained implantable pulse generator having an implanted power source such as a long-lasting or rechargeable battery. Alternatively, IPG 410 may comprise an externally-powered implantable pulse generator receiving at least some of the required operating power from an external power transmitter, preferably in the form of a wireless signal, which may be radio frequency (RF), inductive, etc.

IPG 410 of the illustrated embodiment includes voltage regulator 411, power supply 412, receiver 413, microcontroller (or microprocessor) 414, output driver circuitry 415, and clock 416, as are described in further detail below. Power supply 412 provides a source of power, such as from battery 421 (battery 421 may comprise a non-rechargeable (e.g., single use) battery, a rechargeable battery, a capacitor, and/or like power sources), to other components of IPG 410, as may be regulated by voltage regulator 411. Charge control 422 of embodiments provides management with respect to battery 421. Receiver 413 of embodiments provides data communication between microcontroller 414 and controller 442 of external programmer/controller 440, via transmitter 441. It should be appreciated that although receiver 413 is shown as a receiver, a transmitter and/or transceiver may be provided in addition to or in the alternative to receiver 413, depending upon the communication links desired. Receiver 413 of embodiments, in addition to or in the alternative to providing data communication, provides a conduit for delivering energy to power supply 412, such as where RF or inductive recharging of battery 421 is implemented. Microcontroller 414 provides control with respect to the operation of IPG 410, such as in accordance with a program provided thereto by external programmer/controller 440. Output driver circuitry 415 generates and delivers pulses to selected ones of electrodes 432-435 under control of microcontroller 414. For example, voltage multiplier 451 and voltage/current control 452 may be controlled to deliver a constant current pulse of a desired magnitude, duration, and frequency to a load present with respect to particular ones of electrodes 432-435. Clock 416 preferably provides system timing information, such as may be used by microcontroller 414 in controlling system operation, as may be used by voltage multiplier 451 in generating a desired voltage, etc.

Lead 430 of the illustrated embodiment includes lead body 431, preferably incarcerating a plurality of internal conductors coupled to lead connectors (not shown) to interface with lead connectors 453 of IPG 410. Lead 430 further includes electrodes 432-435, which are preferably coupled to the aforementioned internal conductors. The internal conductors provide electrical connection from individual lead connectors to each of a corresponding one of electrodes 432-435. In the exemplary embodiment the lead 430 is generally configured to transmit one or more electrical signals from IPG 410 for application at, or proximate to, a spinal nerve or peripheral nerve, brain matter, muscle, or other tissue via electrodes 432-435. IPG 410 is capable of controlling the electrical signals by varying signal parameters such as intensity, duration and/or frequency in order to deliver a desired therapy or otherwise provide operation as described herein.

Although the embodiment illustrated in FIG. 4 includes 4 electrodes, it should be appreciated that any number of electrodes, and corresponding conductors, may be utilized according to some embodiments. Moreover, various types, configurations and shapes of electrodes (and lead connectors) may be used according to some embodiments. An optional lumen (not shown) may extend through the lead 430, such as for use in delivery of chemicals or drugs or to accept a stylet during placement of the lead within the body. Additionally or alternatively, the lead (stimulation portion) and IPG (generator portion) may comprise a unitary construction, such as that of a microstimulator configuration.

As mentioned above, external programmer/controller 440 of embodiments provides data communication with IPG 410, such as to provide control (e.g., adjust stimulation settings), provide programming (e.g., alter the electrodes to which stimulation pulses are delivered), etc. Accordingly, external programmer/controller 440 of the illustrated embodiment includes transmitter 441, for establishing a wireless link with IPG 410, and controller 442, to provide control with respect to programmer/controller 414 and IPG 410. Additionally or alternatively, external programmer/controller 440 may provide power to IPG 410, such as via RF transmission by transmitter 441. Optionally, however, a separate power controller may be provided for charging the power source within IPG 410.

Additional detail with respect to pulse generation systems and the delivery of stimulation pulses may be found in U.S. Pat. No. 6,609,031, entitled "MULTIPROGRAMMABLE TISSUE STIMULATOR AND METHOD," the disclosure of which is hereby incorporated herein by reference. Similarly; additional detail with respect to pulse generation systems and the delivery of stimulation pulses may be found in the above referenced patent application entitled "MULTI-PROGRAMMABLE TRIAL STIMULATOR."

Having generally described stimulation system 400 above, the discussion which follows provides detail with respect to various functional aspects of stimulation system 400 according to some embodiments. Although the below embodiments are described with reference to stimulation system 400, and IPG 410 thereof, it should be appreciated that the inventive concepts described herein are not limited to application to the exemplary system and may be used in a wide variety of medical devices.

Voltage Multiplier Output Voltage

Figure 5:
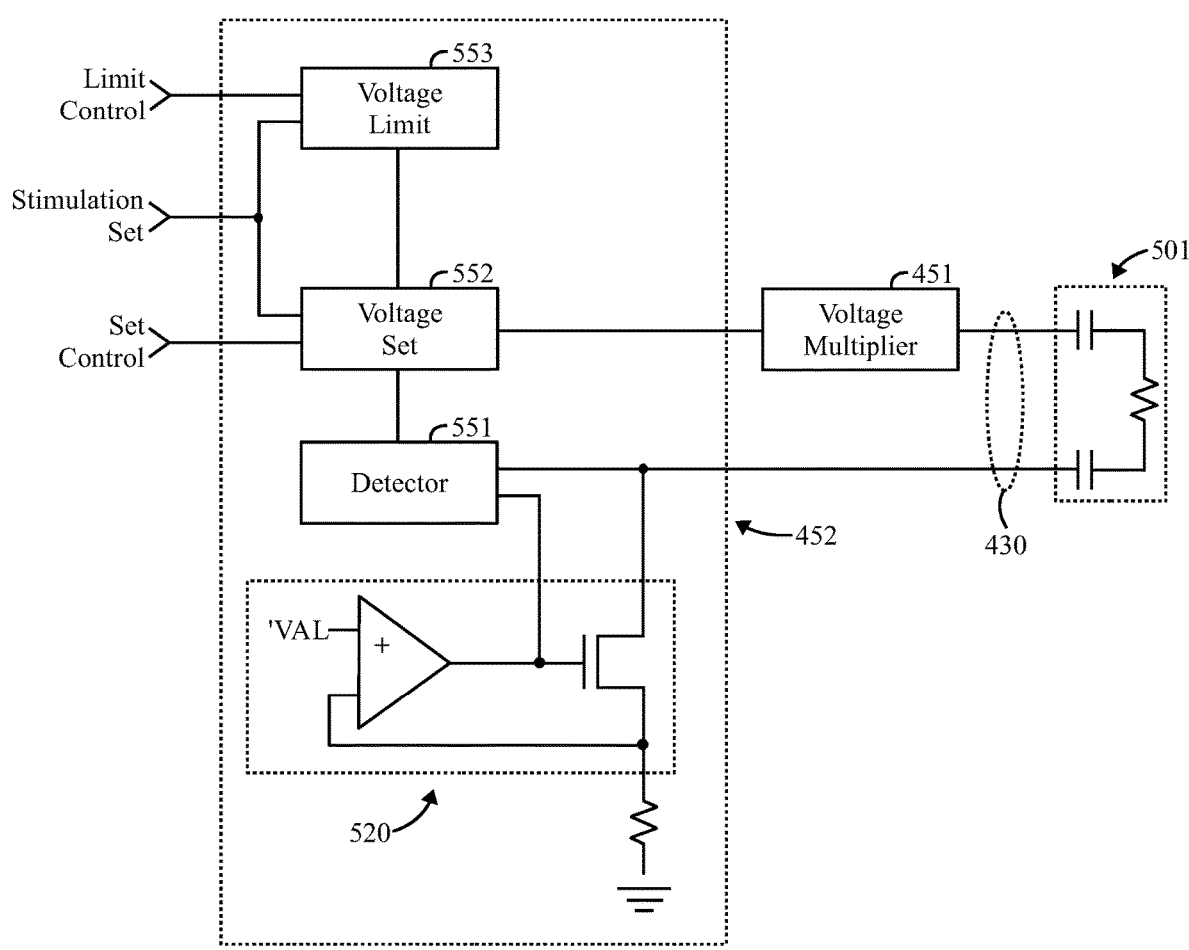
FIG. 5 illustrates detail with respect to an embodiment of voltage/current control of FIG. 4 for providing voltage multiplier voltage control is shown.

Directing attention to FIG. 5, detail with respect to an embodiment of voltage/current control 452 of FIG. 4 for providing voltage multiplier voltage control is shown. Voltage/current control 452 of the illustrated embodiment provides automatic and manual voltage control, allowing incrementing and decrementing of the output voltage, with respect to voltage multiplier 451. In a manual mode of one embodiment, the output voltage setting is controlled by microcontroller 414 providing a set control signal to voltage/current control 452. Accordingly, in this manual mode, microcontroller 414 is involved in the changes to the output voltage of voltage multiplier 451 in terms of incrementing or decrementing the values. However, in an automatic mode of one embodiment, voltage/current control 452 controls the changes to the output voltage of voltage multiplier 451, and thus there need not be any processing overhead on the part of microcontroller 414 to determine the optimal value for the output voltage of voltage multiplier 451.

Voltage multiplier 451 utilized according to some embodiments preferably comprises a fractional voltage multiplier, such as may provide output voltages in fractional multiples of a supply voltage. Additional detail with respect to fractional voltage multipliers as may be utilized according to some embodiments is provided in U.S. Pat. No. 7,180,760 entitled "FRACTIONAL VOLTAGE CONVERTER", filed Apr. 12, 2005, the complete subject matter of which is expressly incorporated herein by reference. In operation of IPG 410 according to some embodiments, a goal is to provide a power source to deliver a particular amount of current to load 501 (such as may comprise a portion of a human body into which lead 430 is implanted) via selected ones of electrodes 432-435. It should be appreciated that, as set forth in Ohm's law, a particular amount of voltage provided by voltage multiplier 451 will be needed to deliver a desired level of current through load 501. However, providing a voltage level substantially in excess of the voltage needed to deliver the desired current may be undesirable. For example, voltage in excess to that needed for delivery of the desired current may be dissipated as heat or otherwise sunk, thereby resulting in inefficient use of energy from battery 421. Moreover, if the output voltage provided by voltage multiplier 451 were not set to a limit somewhat near that needed to deliver the desired current, a change in load 501 (such as by movement of lead 130 within the patient) could result in over stimulation or other undesired results.

As explained herein, the lead 330 includes an EMI antenna that is utilized to sense and mitigate interference voltages induced by EMI. By way of example, the EMI antenna may include one or more Kelvin connect electrodes or unused electrodes (e.g., any one or more of the electrodes) that are not being used to deliver stimulation therapy to the patient. Additionally or alternatively, the EMI antenna may be constructed as a "dummy" wire provided within the lead or routed with insulation substantially alongside the outside of the lead and arranged to extend alongside other stimulation wires in the lead. The dummy wire may not touch human tissue, and thus may not be considered to be an "electrode."

Accordingly, voltage multiplier 451 and voltage/current control 452 of some embodiments cooperate to provide a voltage limited, constant current source. In providing the foregoing, voltage/current control 452 of the illustrated embodiment comprises detector 551 that monitors voltages as provided by voltage multiplier 451. When it is determined that the output voltage of voltage multiplier 451 is in excess (perhaps by a predetermined amount, such as a fractional voltage step amount) of what is needed to provide a desired current, detector 551 can provide a control signal to voltage set 552 to decrement the voltage. Voltage set 552 may, in turn, provide a control signal to voltage multiplier 451 to select an appropriate, lower, voltage (perhaps in one or more decremental steps). Similarly, when it is determined that the output voltage of voltage multiplier 451 is below what is needed to provide a desired current, detector 551 can provide a control signal to voltage set 552 to increment the voltage. Voltage set 552 may, in turn, provide a control signal to voltage multiplier 451 to select an appropriate, higher, voltage (perhaps in one or more incremental steps). Feedback circuit 520 provides detail with respect to providing information to detector 551 useful in making voltage increment/decrement determinations. The voltage limit 553 sets a limit beyond which voltage/current control 452 cannot, by itself increment the output voltage. Accordingly, when a voltage limit set by voltage limit 553 is reached, voltage/current control 452 may provide a control signal to microcontroller, such as to notify an operator of the limit being reached, for a determination with respect to whether the limit should be adjusted, etc.

Additionally, microcontroller, a clinician, or other user may manually provide voltage selection with respect to voltage multiplier 451, such as during trial stimulation, etc. Accordingly, a voltage set control signal may be provided to voltage set 552, such as by microcontroller, to override voltage selection as provided by detector 551, if desired.

Current Regulation Circuit

Figure 6A:
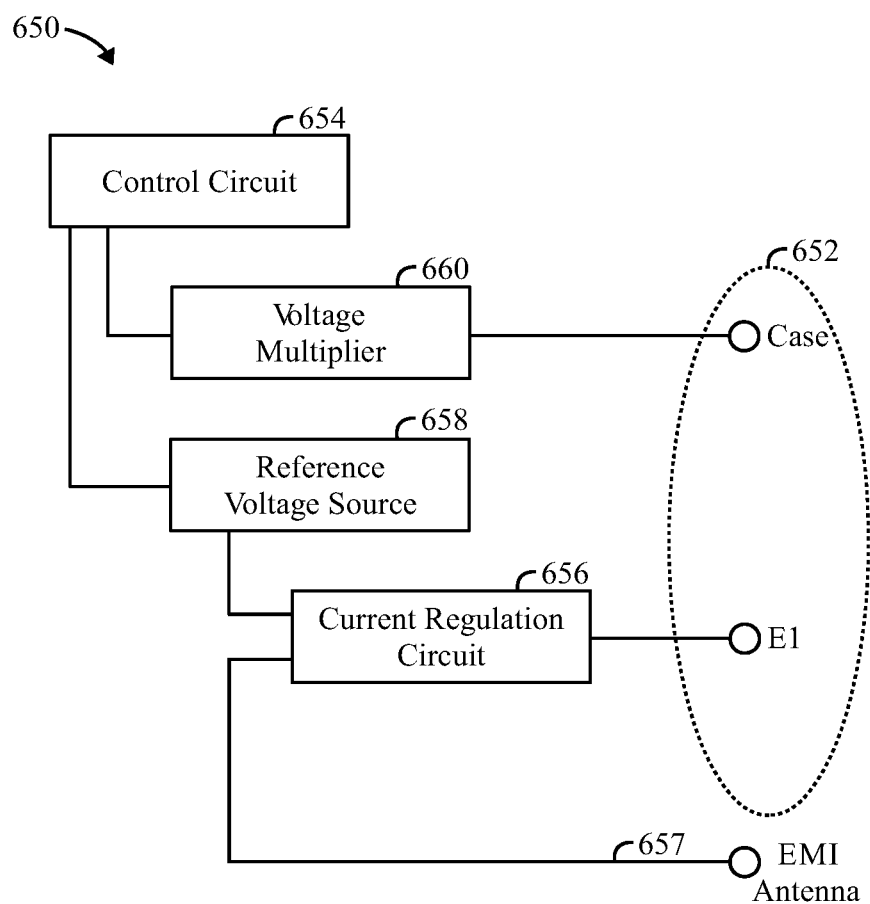
FIG. 6A illustrates a block diagram of therapy and discharge control circuits of an NS system utilized in accordance with embodiments herein.

FIG. 6A illustrates a block diagram of therapy and discharge control circuits of an NS system utilized in accordance with embodiments herein. The neurostimulation (NS) system 650 comprises an array of electrodes 652 configured to be implanted within a patient and positioned proximate to neural tissue of interest that is associated with the target region. As a nonlimiting example, the NS system may be configured for use with deep brain stimulation, with the array of electrodes positioned within the brain proximate to neural tissue of interest. The array of electrodes 652 includes one or more active electrodes E1. The one or more active electrodes E1 represent a cathode. The NS system 650 also includes a Case electrode which may be configured to be an anode electrode. Optionally, an electrode from the array of electrodes 652 may be configured to operate as the anode electrode. While the examples herein are described in connection with a single electrode E1 as the active electrode used as a cathode, it is recognized that in many embodiments, two or more active electrodes may be utilized. When two or more active electrodes E1 are utilized, embodiments herein may implement discharge operations in the presence of EMI events in a common discharge operation, and/or as separate discharge operations. For example, all active electrodes E1 may be connected to one another during the discharge operation in a common manner to collectively and jointly discharge any residual voltage. As another example, separate subsets of the group of active electrodes E1 may be connected to separate current regulator circuits to have residual voltages discharged separately.

The array of electrodes may include one or more inactive electrodes Ea One or more of the inactive electrodes E0 may be utilized as the EMI antenna to sense and mitigate interference voltages induced by EMI. By way of example, the EMI antenna may include one or more Kelvin connect electrodes in the NS lead that are not being used to deliver stimulation therapy to the patient.

The NS system 650 includes a control circuit 654 that is configured to control delivery of a NS therapy during therapy delivery intervals between the active cathode electrode and the anode electrode. The NS therapy is delivered through the active cathode electrode E1 proximate to neural tissue of interest that is associated with a target region. The array of electrodes 652 develop a residual voltage (e.g., an accumulated charge) over the therapy delivery intervals. The residual voltage is induced/developed between the anode electrode (e.g., CASE) and the active cathode electrode(s) over the course of the NS therapy.

A current regulator (CR) circuit 656 is connected to the active cathode electrode E1. The CR circuit 656 is configured to control current flow through the cathode electrode E1. The control circuit 654 is coupled to the CR circuit 656 and, during the discharge operation, the control circuit 654 is configured to manage the CR circuit 656 to control the discharge current flow over the discharge operation to discharge the residual voltage in a manner that follows the AEPD profile between the therapy delivery intervals.

While embodiments herein are described in connection with the use of a single AEPD profile, it is recognized that more than one AEPD profile may be utilized. For example, when an NS therapy delivers different types of stimulation to different combinations of electrodes, different residual voltages may build up upon the corresponding combinations of electrodes. Accordingly, a separate AEPD profile may be assigned in connection with each combination of electrodes for the corresponding residual voltage.

By way of example, the AEPD profile may be managed in accordance with the methods and systems described in a co-pending application Ser. No. 16/364,975 filed Mar. 26, 2019, entitled "EMULATING PASSIVE DISCHARGE OF ELECTRODES USING A PROGRAMMABLE EXPONENTIALLY DECREASING AMPLITUDE DISCHARGE CURRENT", the complete subject matter of which is expressly incorporated herein by reference in its entirety.

During the discharge operation, the CR circuit 656 is connected to an EMI antenna 657. The CR circuit 656 receives, as a first input, an electromagnetic interference (EMI) feedback signal from the EMI antenna 657 and regulates the discharge current flow through the active electrodes based on the EMI feedback signal to maintain the AEPD profile over the discharge operation even while in the presence of an EMI event. The EMI feedback signal is indicative of a voltage gradient created at the EMI antenna 657 based at least in part on an electromagnetic field surrounding the NS system. As explained hereafter, the CR circuit 656 may comprise an error amplifier and a transistor. The error amplifier is configured to hold the EMI feedback signal at a reference voltage and provide an output based thereon, while the transistor is configured to regulate the discharge current flow through the active electrodes based on the output of the error amplifier to maintain the AEPD profile while in the presence of the EMI event.

The NS system 650 further comprises a reference voltage source 658 that is configured to supply a reference voltage signal as a second input to the CR circuit 656. The CR circuit 656 regulates the current flow through the cathode electrode (E1) based on a difference between the EMI feedback signal and the reference voltage signal. A voltage multiplier 660 is connected to, and controlled by, the control circuit 654. The voltage multiplier 660 defines an output voltage of the NS system 650 when delivering the NS therapy. The control circuit 654, CR circuit 656, reference voltage source 658 and voltage multiplier 660 are hermetically sealed within the housing of an IPG.

The EMI antenna 657 and the active cathode electrode E1 may be configured to have substantially similar electrical properties. The signal from the EMI antenna 657 is supplied to the CR circuit 656 to allow the CR circuit 656 to manage discharge of residual voltage built up across the load of the IPG after stimulation. The CR circuit 656 manages discharge of the residual voltage such that the AEPD profile of the discharge is substantially similar to the discharge profile exhibited during a passive discharge operation.

While the present example is described in connection with delivery of a single series of stimulation pulses, followed by a single discharge interval, it is understood that the control circuit 654 is configured to deliver the NS therapy repeatedly over successive therapy delivery intervals that are separated by corresponding successive discharge operations while in the presence of the EMI event. The CR circuit 656 is configured to modulate the discharge current flow over one or more of the discharge operations, based on the EMI feedback signal, in order to follow a common or multiple AEPD profiles to compensate for voltage fluctuation caused by the EMI event.

In accordance with embodiments herein, the NS system 650 does not need to be programmed with a particular discharge profile and does not require any prior knowledge of the level of the residual voltage across the load after stimulation. Also, the NS system 650 does not need model parameters for the load to effectively and efficiently discharge the load with an exponential decreasing discharge current that closely emulates or mimics the discharge current during a passive discharge operation.

The NS system 650 maintains a high impedance electrical loop between the IPG case and the active stimulation electrode(s) during a patient MRI scan and/or when subject to other types of EMI, to minimize stimulation interference and other concerns. By achieving a high impedance electrical loop behavior during discharge, the CR circuit 656 is able to manage an AEPD operation after stimulation while avoiding degradation of patient therapy from EMI. The CR circuit 656 also mitigates patient safety concerns while allowing stimulation therapy to be continuously delivered during an MRI scan and/or in the presence of other EMI events. Other benefits of the embodiments herein include: 1) alleviating a need for a large amount of IPG memory, which would otherwise be necessary to store numerous digital parameters or values (e.g., the digital representation of the amplitude settings for the CR circuit) to control an exponentially decreasing discharge current; 2) alleviating a need for a complex digital state machine, which would otherwise be necessary to control the timing and reading of parameters for controlling the discharge current; 3) alleviating a need for extracting a model for the IPG load, which would otherwise be necessary to determine the control parameters for emulating passive discharge; 4) eliminating the effects of model errors which could introduce undesirable stimulation artifacts or could further degrade stimulation efficiency or efficacy; and 5) alleviating the need for an extensive number of calculations needed for computing the control parameters required for the CR circuit to otherwise emulate passive discharge.

Figure 6B:
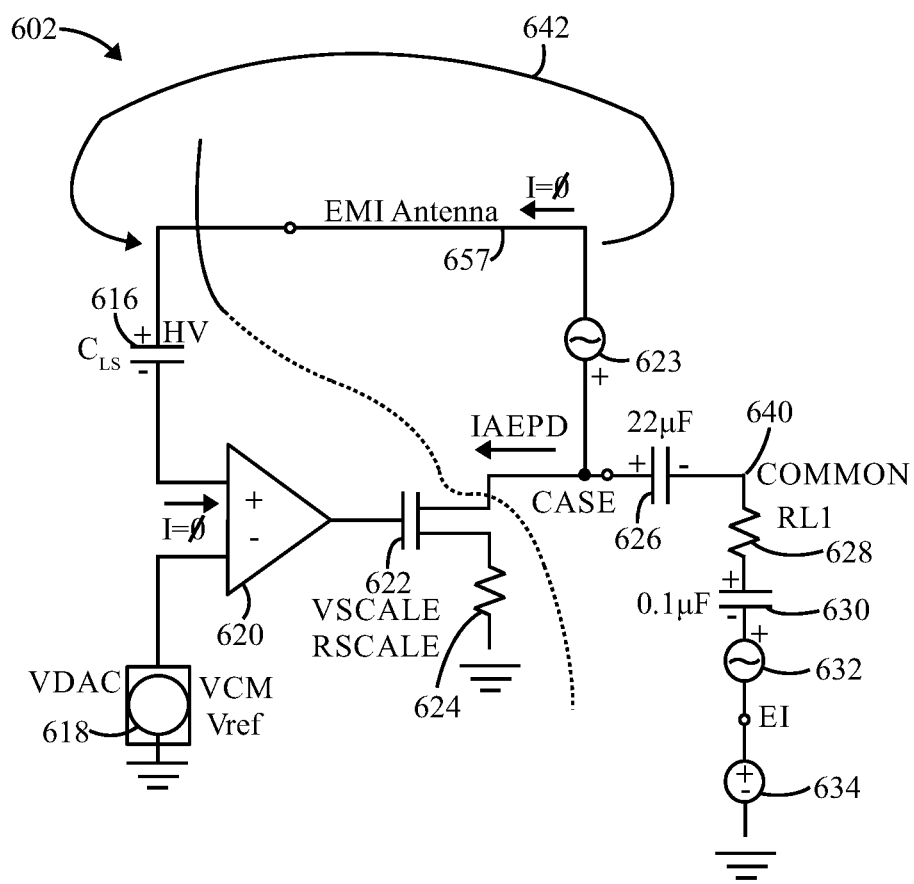
FIG. 6B illustrates a more detailed schematic diagram of the block diagram of FIG. 6A when configured in discharge mode to control an AEPD profile formed in accordance with embodiments herein.

FIG. 6B illustrates a more detailed schematic diagram of the block diagram of FIG. 6A formed in accordance with embodiments herein. The CR circuit 602 is shown as configured for post-stimulation discharge to control an actively emulated passive discharge (AEPD) of charge buildup at two or more electrodes while the system is in a presence of MRI/EMI interference. The CR circuit 602 includes an error amplifier 620, an output of which drives the gate of a MOSFET transistor 622. The error amplifier 620 is configured to hold the EMI feedback signal at a reference voltage and provide an output based thereon, while the transistor 622 is configured to regulate the discharge current flow through the active electrodes based on the output of the error amplifier to maintain the AEPD profile while in the presence of the EMI event.

The error amplifier 620 may be implemented as an operational amplifier or other equivalent circuit. The error amplifier 620 is configured to handle moderately large residual voltages that may build up after stimulation. By way of example, a residual voltage of 5-10 V may build up across the load of the NS system after DBS therapy delivery. The transistor 622 is coupled between the case electrode and a variable resistor 624. The transistor 622 regulates discharge current flow from the active electrodes, through the drain and source of the transistor 622 and the variable resistor 624. The transistor 622 regulates the discharge current flow based on the output of the error amplifier 620. The output of the error amplifier 620 varies based on the voltage difference between the input terminals thereof.

During an AEPD operation, one input terminal (e.g., the positive terminal) of the error amplifier 620 is coupled to the EMI antenna 657 through a high voltage (HV) level shift capacitor 616, while the other input terminal (e.g., the negative terminal) of the error amplifier 620 is connected to a common mode voltage reference source 618. The voltage reference source 618 is controlled by the microprocessor or other control circuit to maintain a common mode reference voltage at the input terminal of the error amplifier 620 during the AEPD operation. By way of example, the microprocessor or other control circuit may selectively decrease the reference voltage maintained at the reference source 618 (e.g., through a series of downward voltage steps) over the duration of the AEPD operation. The HV level shift capacitor 616 is configured to absorb large voltages that may be introduced into the circuit. For example, the HV level shift capacitor 616 is configured to offset/absorb a difference between the multiplier voltage VM (which was introduced at the active anode electrode case during stimulation) and the common mode voltage VCM (provided to the negative input terminal of the error amplifier 620). The HV level shift capacitor 616 is coupled to the positive input terminal of the error amplifier 620 at the end of a stimulation phase, which corresponds to the beginning of a discharge phase. Before the HV level shift capacitor 616 is connected to the positive input terminal of the error amplifier 620, the capacitor 616 has already been charged with a desired voltage corresponding to the difference of the multiplier voltage VM and common mode voltage VCM. At the end of the discharge phase, the capacitor 616 is removed from the connection to the positive input terminal of the error amplifier 620, before the next stimulation phase.

The CR circuit 602 is connected to one or more active electrodes E1, the EMI antenna 657 and an IPG housing electrode denoted "Case". The "active" electrodes E1 represent electrodes utilized to deliver stimulation in one or more types of therapy. The EMI antenna 657 is configured to deliver feedback to the error amplifier 620 (e.g., an operational amplifier) regarding MRI/EMI interference experienced at the EMI antenna 657. The feedback may be provided in the form of a voltage fluctuation over time that is caused by the interference. The EMI antenna 657 may have substantially similar dimensions and electrical characteristics as the active electrode E1 such that the EMI antenna 657 is configured to provide substantially the same common mode interference as experienced at the active electrode E1. The EMI antenna 657 may be configured as a "Kelvin connect" electrode for use during AEPD. It should be recognized that the EMI antenna 657 may not "perfectly" cancel out the interference caused by EMI events. However, the EMI antenna 657 will assist in minimizing the deleterious effects of EMI artifacts for DBS therapy applications which utilize the Case as a stimulation electrode, commonly referred to as a monopolar stimulation configuration. Any remaining minor stimulation interference during AEPD caused by mismatched EMI artifacts on different electrodes is typically within tolerance ranges of conventional systems, without the need for the burdensome bipolar configuration IPG programming solutions that are commonly necessary to maintain DBS therapy delivery during an MRI scan.

In the example of FIG. 6B, the IPG is exposed to MRI and/or EMI interference, and accordingly, the schematic diagram also models MRI/EMI interference at electrode E1, and at the EMI antenna 657 of the IPG. An interference source 623 is modeled as a voltage source that is introduced at the EMI antenna 657 when the EMI antenna 657 is exposed to MRI/EMI interference. An interference source 632 is similarly modeled as a voltage source or a current source that is introduced at the active electrode E1 when the active electrode E1 is exposed to the MRI/EMI interference. The magnitude of the voltage introduced by the interference sources 623 and 632 fluctuates over time in a substantially similar manner (although not identically) at the active electrode E1 and the EMI antenna 657.

The EMI antenna 657 and active electrode E1 may exhibit certain similar capacitive and resistive characteristics that are also modeled as shown in FIG. 6B. For example, the active electrode E1 may exhibit a resistance 628 of RL1 and a capacitance 630 of 0.1 uF. The EMI antenna 657 may exhibit a similar resistance and a similar capacitance.

Optionally, the EMI antenna 657 may be implemented as an "inactive" or unused electrode. E0 represents electrodes that are not used for stimulation in connection with any type of therapy for the present patient. The electrode E0 may also be referred to as a non-stimulation electrode as no therapy is delivered through the electrode E0. The inactive electrode E0 is configured to deliver feedback to the error amplifier 620 (e.g., an operational amplifier) regarding MRI/EMI interference experienced at the inactive electrode E0. The feedback may be provided in the form of a voltage fluctuation over time that is caused by the interference. The inactive electrode E0 has substantially similar dimensions and characteristics as the active electrode E1 such that the inactive electrode E0 is configured to provide substantially the same common mode interference as experienced at the active electrode E1. The inactive electrode E0 may be configured as a "Kelvin connect" electrode for use during AEPD. It should be recognized that the Kelvin connect electrode may not "perfectly" cancel out the interference caused by EMI events. However, the Kelvin connect electrode will assist in minimizing the deleterious effects of EMI artifacts for DBS therapy applications which utilize the Case as a stimulation electrode, commonly referred to as a monopolar stimulation configuration. Any remaining minor stimulation interference during AEPD caused by mismatched EMI artifacts on different electrodes is typically within tolerance ranges of conventional NS systems, without the need for the burdensome bipolar configuration IPG programming solutions that are commonly necessary to maintain DBS therapy delivery during an MRI scan.

Optionally, when a non-electrode wire is used as the EMI antenna, the wire may also be configured to have similar capacitive and resistive characteristics as the active electrodes E1, E2, such that resistances are substantially similar and the capacitances are substantially similar.

In the example of FIG. 6B, the EMI antenna 657 is implemented as a non-electrode wire that is connected between the Case node and the positive input terminal of the error amplifier 620 through the high voltage level shift capacitor 616. The feedback control loop 642 extends in series through the interference source 623 and high-voltage level shift capacitor 616. Alternatively, if the EMI antenna 657 is implemented as an inactive electrode (e.g. E0) the feedback loop control 642 may be connected between the COMMON node 640 and the high-voltage level shift capacitor 616. The feedback control loop is largely immune to electrical characteristics of the active electrode and the EMI antenna.

FIG. 6B also illustrates a DC blocking capacitor 626 that is modeled in series with the case electrode and a COMMON node 640. The DC blocking capacitor 626 is configured to prevent DC current flow through the Case electrode. During the AEPD operation, as charge is drawn from the Case electrode, a current $i_{AEPD}$ flows from the Case electrode to ground through the transistor 622 and variable resistor 624. The magnitude of the discharge current $i_{AEPD}$ varies over the duration of the AEPD operation in a manner that is controlled by the transistor 622. The active electrode E1 is coupled to a voltage multiplier 634 which is also used during a therapy phase in which stimulation is delivered, during which the voltage multiplier 634 delivers a multiplied voltage VM. The VM voltage may be different during the stimulation therapy and discharge phases.

Figure 7:
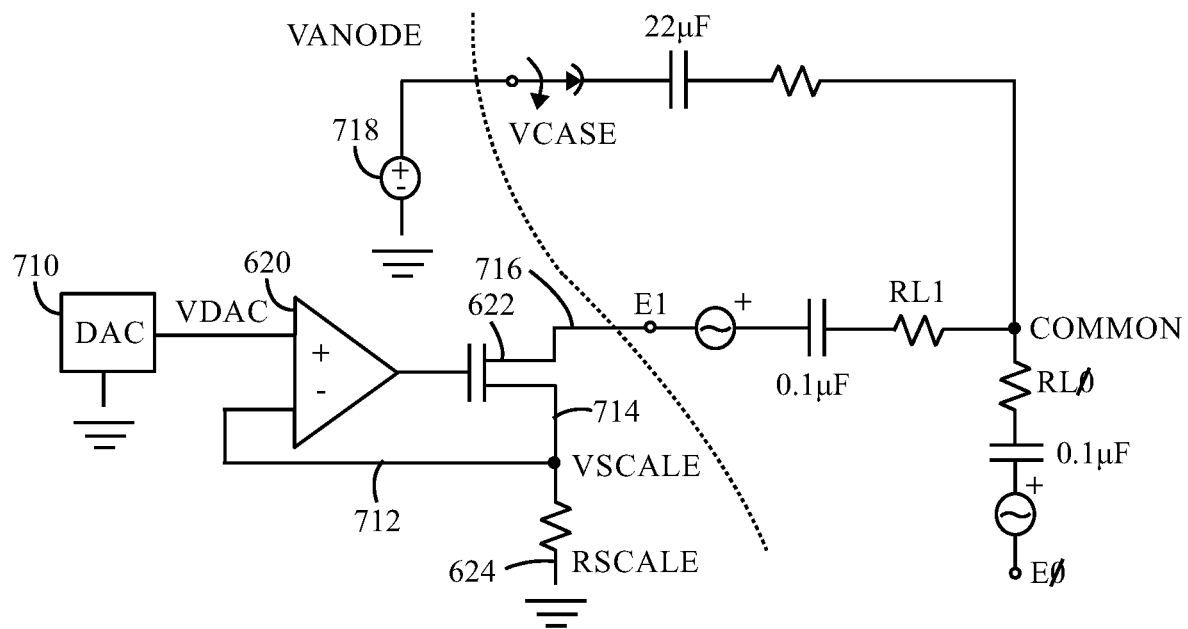
FIG. 7 illustrates a schematic diagram of a portion of the NS system when configured in the stimulation mode.

FIG. 7 illustrates a schematic diagram of a portion of the NS system when switched to the stimulation mode. In the embodiment of FIG. 7, the EMI antenna is implemented as an inactive electrode Ea Once the discharge operation is completed, the NS system switches back to the stimulation mode in which the next stimulus in this therapy may be delivered. In FIG. 7, inputs to the error amplifier 620 are reconfigured for stimulation. The first/positive input is coupled to a digital to analog converter (DAC) 710 that is managed by the control circuit to deliver a series of reference voltages corresponding to the NS therapy. The second/negative input of the error amplifier 620 is connected to node 712 which has the same voltage as the source terminal 714 of the transistor 622. The node 712 is located at the connection of the source terminal 714 of the transistor 622 and the variable resistor 624. The active electrode E1 is connected as a cathode to the drain terminal 716 of the transistor 622, while the electrode CASE is connected as an anode to a voltage multiplier 718. The EMI antenna 657, shown in FIG. 7 implemented as an inactive electrode E0, is disconnected from the error amplifier 620 and is allowed to electrically float, but the EMI antenna 657 can be connected to other circuitry (not shown) for monitoring the interference voltages caused by MRI/EMI. The voltage sources, capacitances and resistances illustrated between the electrode E1, CASE, EMI antenna, and the node denoted COMMON are merely presented to model the electrical characteristics experienced at the electrode E1, CASE, EMI antenna and COMMON node during a stimulation operation.

Figure 8A:
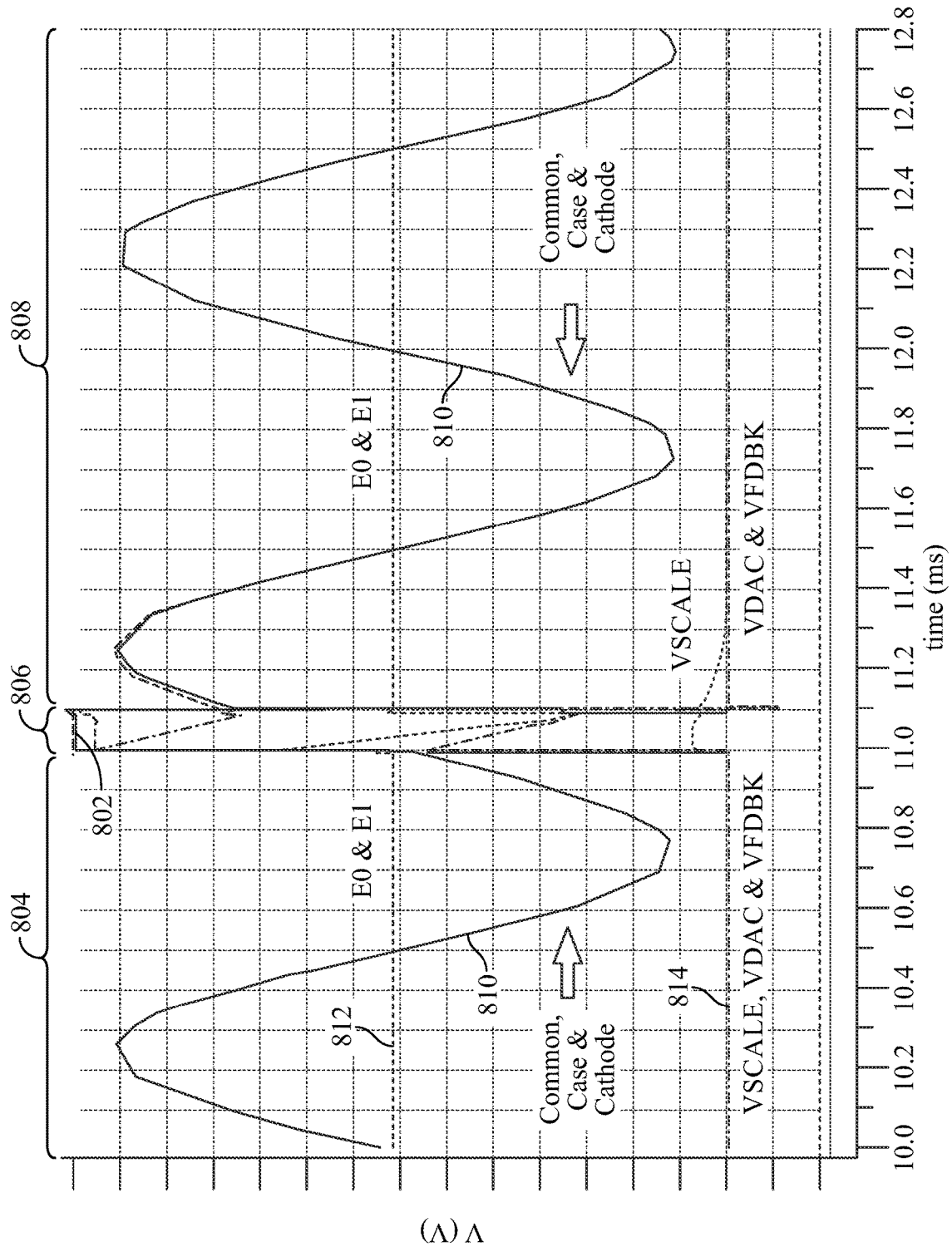
FIG. 8A illustrates an example for voltage potentials experienced at select points in an NS system formed in accordance with embodiments herein before, during and after delivery of an NS therapy in the presence of EMI.

FIG. 8A illustrates an example for voltage potentials experienced at select points in an NS system formed in accordance with embodiments herein before, during and after delivery of an NS therapy in the presence of EMI. The example of FIG. 8A assumes that the EMI antenna is implemented as an inactive electrode Ea By way of example, the timing diagram plots voltage along the vertical axis at various points within the NS system and time along the horizontal axis. In the timing diagram, the stimulation time period 806 corresponds to an interval in which a stimulation current pulse 802 is delivered as part of an NS therapy, while the discharge intervals 804 and 808 corresponded to time periods before and after the stimulation current pulse 802. In the present example, the stimulation current pulse is approximately 90 µs in duration.

Figure 8B:
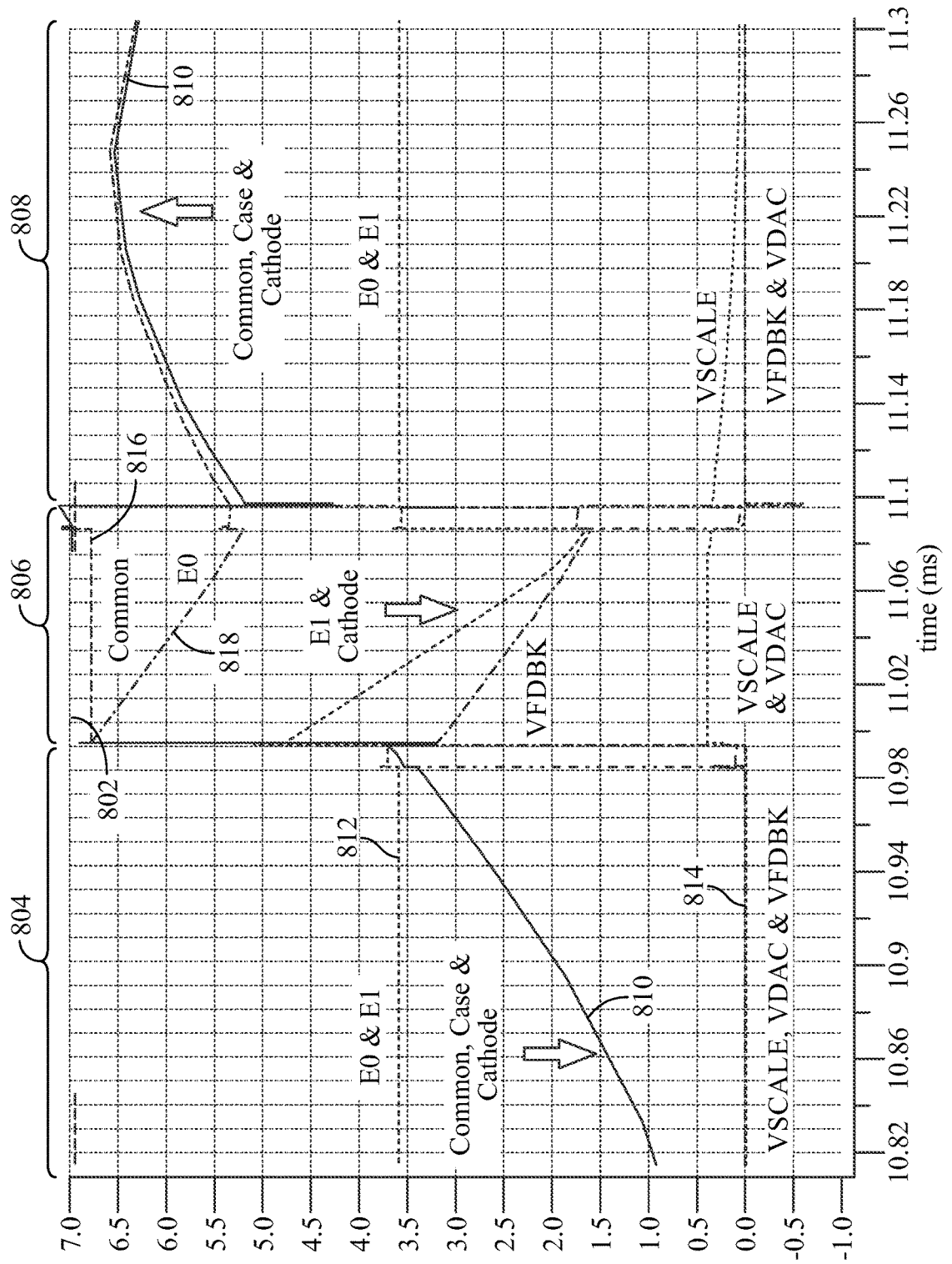
FIG. 8B illustrates an enlarged view of the voltage potentials within the portion of FIG. 8A immediately before, during and immediately after delivery of the stimulation pulse.
Figure 9:
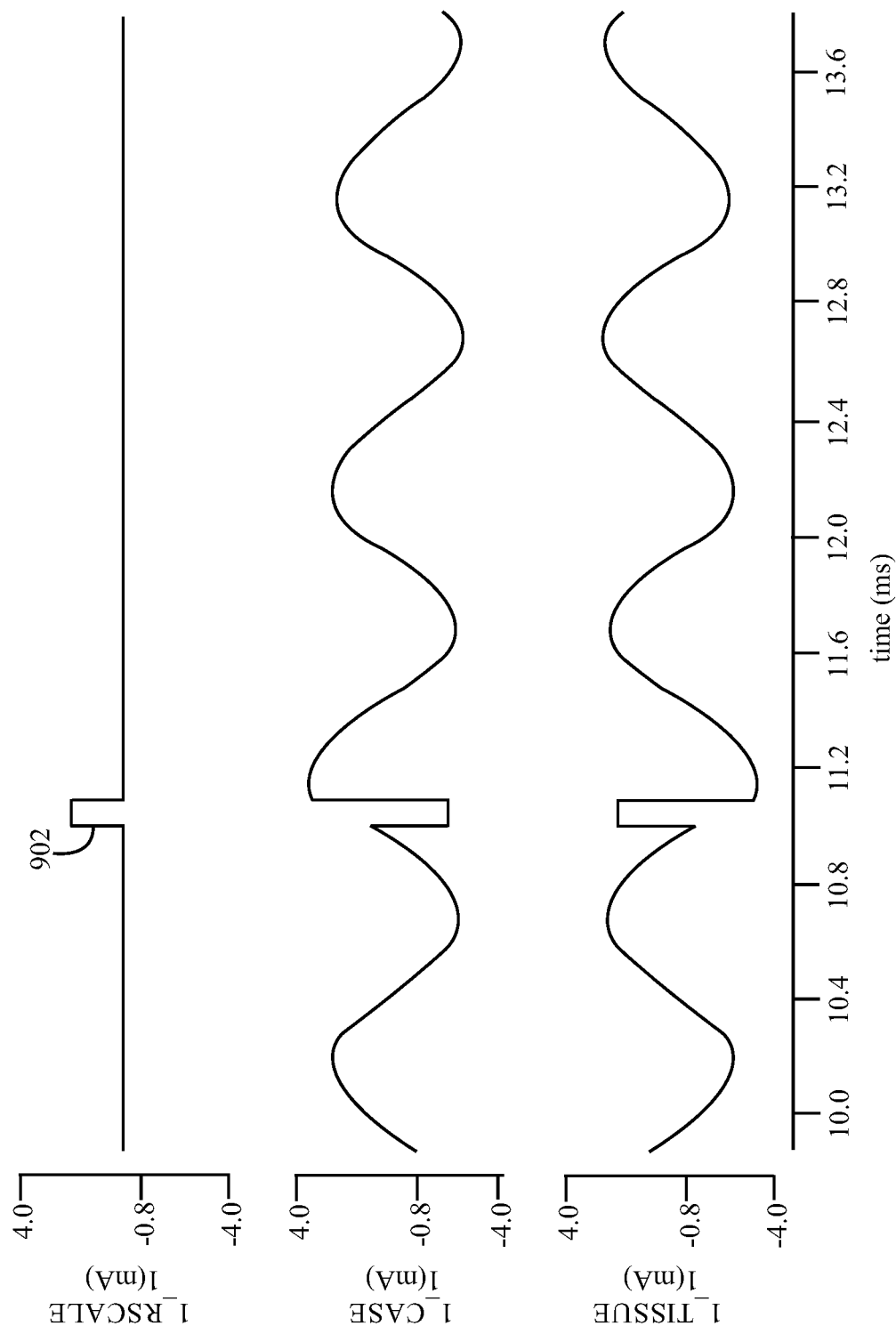
FIG. 9 illustrates an example for current signals flowing at select time points for a conventional IPG that is attempting to deliver an NS therapy using a Monopolar stimulation electrode configuration while in the presence of EMI.

FIG. 8B illustrates an enlarged view of the voltage potentials within the portion of FIG. 8A immediately before, during and immediately after delivery of the stimulation pulse 802. The NS system operates with internal circuitry in the therapy delivery configuration of FIG. 7 during the stimulation time period 806 and operates with the discharge configuration of FIG. 6B during the discharge intervals 804, 808. The NS system alternately operates in the configurations as shown in FIGS. 6B and 7 when it changes between the stimulation interval and discharge intervals.

With reference to FIGS. 6B and 8A, during the discharge intervals 804 and 808, voltage source 634 is fixed at a predetermined voltage and thus maintains the predetermined voltage at electrode E1. In the present example, the voltage source 634 is set to a voltage of 3.6 V and therefore a voltage of approximately 3.6 V is maintained at E1 (as denoted by reference voltage 812) throughout the discharge interval/operation. The interference sources 610 and 632 represent models of voltages introduced by the EMI to cause an EMI-induced voltage 810 to vary in a sinusoidal manner at the nodes denoted COMMON, CASE and CATHODE during the discharge intervals 804 and 808. The COMMON node 640 and CASE node are on opposite sides of DC blocking capacitor 626, while the CATHODE node corresponds to the drain terminal of the MOSFET transistor 622 during stimulation. Outside of stimulation, the EMI causes the voltage at the COMMON node 640 to shift upward and downward to follow the EMI-induced voltage 810, centered at the reference voltage 812. Similarly, outside of stimulation, the voltage at the CASE electrode/node moves up and downward to follow the EMI-induced voltage 810, centered at the reference voltage 812.

During discharge, electrode E0 also maintains a voltage substantially corresponding to the reference voltage at electrode E1, as defined by the voltage source 634. Except for a short time period immediately after stimulation when the discharge current first starts to flow, electrodes E0 and E1 are substantially maintained at the same voltage, corresponding to the voltage source 634, given that the electrodes E0 and E1 experience substantially similar interference voltages (e.g., in phase, frequency and amplitude) which are induced by the EMI, as denoted by substantially similar interference sources 610, 632. To better understand why the nodes E0 and E1 substantially maintain the same voltage, consider the following example. The voltage source 634 defines the voltage at E1. EMI creates a voltage interference, modeled as the interference source 632, which causes the voltage at the COMMON node 640 to move up and down. The voltage at node E0 does not move up and down with the voltage at the COMMON node 640, because the EMI also creates a voltage interference modeled as the interference source 610. The interference source 610 effectively cancels out the voltage fluctuations at the COMMON node 640. It should be noted that the interference sources 610 and 632 are oriented such that a common polarity (e.g., the positive polarity) of both is directed towards the COMMON node 640, while the opposite interference source polarity (e.g., the negative polarity) is directed toward nodes E0 and E1. By utilizing the unused electrode E0 for feedback to the positive input of error amplifier 620 during the discharge operation, the unused electrode E0 substantially cancels out EMI induced current flow during the discharge phase.

Continuing with the signal diagrams of FIG. 8A, a voltage 814 during discharge phase 804 is maintained at nodes denoted VFDBK (e.g., feedback voltage), VDAC and VSCALE immediately prior to stimulation. The VFDBK node corresponds to the positive input terminal of the error amplifier 620, the VDAC node corresponds to the output of the voltage reference source 618, and the VSCALE node corresponds to the voltage across the resistor 624. During discharge phase 808 immediately after stimulation, the voltages at nodes VDAC and VFDBK remain substantially the same as during the discharge phase 804, but node VSCALE exhibits an exponentially decreasing voltage characteristic which is consonant with the flow of the intended AEPD current.

Turning to FIG. 8B, the voltage signals during the discharge intervals 804 and 808 correspond to the signals described in connection with FIG. 8A. During a stimulation time period 806, the voltages at the various nodes (e.g., CASE, COMMON, E0, E1, CATHODE, VFDBK, VSCALE, and VDAC) differ as noted in FIG. 8B. During delivery of a stimulation pulse 802, the COMMON node 640 is substantially held to a constant voltage noted at 816. At the beginning of a stimulation pulse, the electrode E0 has a voltage substantially similar to the voltage at the COMMON node 640 but decreases over time along an inverse ramp 818 over the duration of the stimulation pulse. By way of example, the rate at which the voltage at E0 decreases may generally represent an inverse of a rate of increase in the EMI-induced voltage. During the stimulation phase 806, the voltage at node E1 begins at a voltage level below the voltage at node COMMON which corresponds to the IR voltage drop across E1 electrode resistance RL1, then the voltage at node E1 decreases over the course of the stimulation pulse as current is delivered (due to the build-up of charge on the 0.1 uF electrode/tissue interface capacitance associated with electrode E1).

The methods and systems described herein are utilized generally in connection with monopolar stimulation techniques, in which the IPG CASE is utilized as an electrode. Closing It may be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer," "subsystem," "controller circuit," "circuit," or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "controller circuit".

The computer, subsystem, controller circuit, circuit execute a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer, subsystem, controller circuit, and/or circuit to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A system, comprising:
   a plurality of electrodes positioned within a patient, the plurality of electrodes including an active electrode, the active electrode configured to be a cathode electrode located proximate to tissue of interest that is associated with a target region;
   an anode electrode;
   an antenna;

a control circuit configured to control delivery of a therapy during a therapy delivery interval, the therapy to be delivered between the anode electrode and the active electrode, the system developing a residual charge between the anode electrode and the active electrode over the therapy delivery interval;

a regulator circuit connected to the cathode electrode, the regulator circuit configured to control at least one of voltage or current at the cathode electrodes;

during a discharge operation, the control circuit configured to manage the CR circuit to control at least one of a discharge voltage or current over the discharge operation to discharge the residual charge after therapy delivery in a manner that follows an actively emulated passive discharge (AEPD) profile; and during the discharge operation, the regulator circuit configured to regulate at least one of the discharge voltage or current through the active electrode based on an electromagnetic interference (EMI) feedback signal, to maintain the AEPD profile over the discharge operation while in a presence of an EMI event.

2. The system of claim 1, wherein the antenna is an EMI antenna is configured to generate the EMI feedback signal indicative of a voltage interference induced at least in part by an electromagnetic field surrounding the system.

3. The system of claim 1, wherein the antenna includes at least one of: i) an inactive electrode, and ii) a non-electrode wire within a lead or routed with insulation substantially alongside the outside of the lead, having the array of electrodes provided at a distal end of a lead.

4. The system of claim 1, further comprising a reference voltage source configured to supply a reference voltage as a second input to the regulator circuit, the regulator circuit configured to regulate at least one of the discharge voltage or current through the active and anode electrodes based on a difference between the EMI feedback signal and the reference voltage.

5. The system of claim 1, wherein the regulator circuit comprises an error amplifier and a transistor, the error amplifier configured to hold the EMI feedback signal at a reference voltage and provide an output based thereon, the transistor configured to regulate the current flow through the active and anode electrodes based on the output of the error amplifier to maintain the AEPD profile while in the presence of the EMI event.

6. The system of claim 1, wherein the antenna includes an inactive electrode, and wherein the inactive electrode and the active electrode are configured to have substantially similar electrical properties.

7. The system of claim 1, further comprising a lead having a distal end that includes the plurality of electrodes, the antenna including a non-electrode wire within the lead or a wire routed with insulation substantially alongside the outside of the lead.

8. The system of claim 1, wherein the antenna is configured to sense and mitigate interference from EMI.

9. The system of claim 1, wherein the control circuit is configured to deliver a neurostimulation (NS) therapy as the therapy.

10. The system of claim 1, wherein the regulator circuit is configured to modulate the current flow over the discharge operation, based on the EMI feedback signal, in order to follow the AEPD profile to compensate for voltage fluctuation caused by the EMI event.

11. A method, comprising:
providing a plurality of electrodes to be located proximate to tissue of interest that is associated with a target region, the plurality of electrodes including an active electrode configured to be a cathode electrode;

delivering a therapy during a therapy delivery interval between an anode electrode and the active electrode, the system developing a residual charge between the anode electrode and the active electrode over the therapy delivery interval; and during a discharge operation in a presence of an EMI event:
controlling at least one of a discharge voltage or current over the discharge operation to discharge the residual charge after therapy delivery in a manner that follows an actively emulated passive discharge (AEPD) profile;

obtaining an electromagnetic interference (EMI) feedback signal from an antenna while in the presence of the EMI event; and regulating the at least one of a discharge voltage or current at the anode and cathode electrodes based on the EMI feedback signal to maintain the AEPD profile over the discharge operation while in the presence of the EMI event.

12. The method of claim 11, wherein the EMI feedback signal is indicative of a voltage interference induced at least in part by an electromagnetic field surrounding the system.

13. The method of claim 12, wherein the voltage gradient is induced between the antenna and the anode electrode.

14. The method of claim 11, further comprising supplying a reference voltage, and regulating the current flow based on a difference between the EMI feedback signal and the reference voltage.

15. The method of claim 11, wherein the controlling operation further comprises:
utilizing a regulator circuit that comprises an error amplifier and a transistor;
comparing the EMI feedback signal to a reference voltage at the error amplifier and provide an output based thereon; and
utilizing the transistor to regulate the discharge current flow through the anode and cathode electrodes based on the output of the error amplifier to maintain the AEPD profile while in the presence of the EMI event.

16. The method of claim 11, further comprising utilizing an inactive electrode as the antenna and configuring the inactive electrode and the active electrode to have substantially similar electrical properties.

17. The method of claim 11, further comprising implanting a lead having a distal end that includes the plurality of electrodes and utilizing a non-electrode wire within the lead or a wire routed with insulation substantially alongside an outside of the lead as the EMI antenna.

18. The method of claim 11, further comprising implanting an implantable pulse generator that houses a control circuit and current regulator (CR) circuit that deliver a neurostimulation (NS) therapy as the therapy.

19. The method of claim 18, wherein the delivering operation further comprises delivering the NS therapy repeatedly over successive therapy delivery intervals that are separated by corresponding successive discharge operations while in the presence of the EMI event.

20. The method of claim 19, wherein the regulating operation further comprises compensating for voltage fluctuation caused by the EMI event by modulating the discharge current flow over the discharge operation, based on the EMI feedback signal, in order to follow the AEPD profile.

\* \* \* \* \*